United States Patent [19]

Innis et al.

[11] Patent Number: 5,045,463

[45] Date of Patent: Sep. 3, 1991

[54] DNA EXPRESSION VECTOR AND USE THEREOF

[75] Inventors: Michael A. Innis; David H. Gelfand, both of Oakland; James H. Meade, Pinole, all of Calif.

[73] Assignee: Cetus Corporation, Emeryville, Calif.

[21] Appl. No.: 287,688

[22] Filed: Dec. 19, 1988

Related U.S. Application Data

[63] Continuation of Ser. No. 563,941, Dec. 20, 1983, abandoned.

[51] Int. Cl.$^5$ .............. C12N 9/34; C12N 1/16; C12N 1/18; C12N 15/00; C12P 21/00; C12P 7/06; C07H 21/04

[52] U.S. Cl. .............. 435/205; 435/69.1; 435/69.8; 435/71.1; 435/71.2; 435/161; 435/255; 435/256; 435/320; 536/27; 935/14; 935/48; 935/69

[58] Field of Search .............. 435/68, 70, 91, 172.1, 435/172.3, 252.3, 252.31-252.35, 254, 255, 256, 205, 914, 320, 161, 69.1, 69.8, 71.1, 71.2; 536/27; 935/14, 68, 70, 72, 73, 74, 29, 19, 21, 69

[56] References Cited

U.S. PATENT DOCUMENTS

| | | | |
|---|---|---|---|
| 3,418,211 | 12/1968 | Van Lanen et al. | 435/165 |
| 3,660,236 | 5/1972 | Dworschack et al. | 435/914 |
| 4,374,198 | 2/1983 | Miller et al. | 435/162 |
| 4,411,994 | 10/1983 | Gilbert et al. | 435/172.3 |
| 4,536,477 | 8/1985 | Katkocin et al. | 435/205 |

FOREIGN PATENT DOCUMENTS

| | | |
|---|---|---|
| 0012494 | 6/1980 | European Pat. Off. |
| 0034470 | 8/1981 | European Pat. Off. |
| 0060057 | 9/1982 | European Pat. Off. |
| 0068646 | 1/1983 | European Pat. Off. |
| 0088632 | 9/1983 | European Pat. Off. |
| 2068969 | 8/1981 | United Kingdom . |

OTHER PUBLICATIONS

Yamashita et al., *Agric. Biol. Chem.*, 47, (11), 2689–2692, (1983).

Rutter, "Production of 'Valuable' Proteins in Alternate Biological Hosts", in *Recombinant DNA and Genetic Experimentation*, pp. 123–128, (J. Morgan and W. J. Whelan, eds., 1979).

Hitzeman et al.; *Nature*, 293:717, (1981).

Okazaki et al., "Preferential Synthesis of Extracellular Glucoamylase by *Aspergillus niger*: Stability of mRNA Associated with Membrane-Bound Polysomes in Nongrowing Mycelia", *J. Ferment. Technol.*, 56:279, (1978).

Houghton et al., "The Complete Amino Acid Sequence of Human Fibroblast Interferon as Deduced Using Synthetic Oligodeoxyribonucleotide Primers of Reverse Transcriptase", *Nucleic Acids Res.*, 8:2885, (1980).

Helling et al., "The Molecular Cloning of Genes—General Procedures", in *Genetic Engineering*, Chakrabarty, (ed.), CRC Press, Inc., 1978, pp. 1–30.

(List continued on next page.)

*Primary Examiner*—James Martinell
*Attorney, Agent, or Firm*—Irell & Manella

[57] ABSTRACT

A gene having a DNA sequence complementary to that of the glucoamylase polypeptide mRNA from a fungal species, preferably *Aspergillus awamori*, is prepared. The mRNA is an approximately 2.2 kilobase poly A RNA obtained from fungal cells grown under conditions of glucoamylase induction. Reverse transcription of the mRNA provides a glucoamylase probe used to identify genomic digest fragments containing glucoamylase gene regions, which are sequenced to locate the introns and exons. The genomic fragments are spliced together to form a gene having a DNA sequence with altered or deleted introns which codes for fungal glucoamylase protein and is capable, when correctly combined with a cleaved DNA expression vector, of expressing a non-native protein having glucoamylase enzyme activity upon transformation of a host organism by the vector. The host is preferably bacteria or yeast. The transformed yeast host may be used to produce ethanol.

38 Claims, 16 Drawing Sheets

OTHER PUBLICATIONS

Rosenberg et al., "Regulatory Sequences Involved in the Promotion and Termination of RNA Transcription", Ann. Rev. Genet., 13:319, (1979).

Maxam et al., "A New Method for Sequencing DNA", Proc. Natl. Acad. Sci. USA, 74:560, (1977).

*Biological Science*, Second Ed., 1972, Keeton, W. W. Norton & Co., Inc., New York, pp. 738-742.

Kinnaird, J. H. et al., *Gene*, 20, 387, (1982).

Shoemaker et al., *Biotechnology*, vol. 1, #8, (Oct. 1983), pp. 691-696.

Svensson, B. et al., *Carlsberg Res. Commun.*, 47, p. 55, (1982).

Tubb et al., *Curr. Dev. Yeast Res.*, 5th ed., 75-79, (1981), (Proc. Int. Yeast Symp.).

Erratt et al., *Curr. Dev. Yeast Res.*, 5th ed., 177-183, (1981), (Proc. Int. Yeast Symp.).

*Biotechnology News*, vol. 2, No. 19, (Oct. 1, 1982), p. 2, concerning work of P. Rogers, School of Biotechnology, Sydney, Australia.

Poster Session at Cetus-UCLA Symposium on Gene Expression, (Mar. 26 to Apr. 1, 1983) in Park City, Utah.

Poster Session at ASM Conference on Gene Manipulations in the Exploitation and Study of Fungi, (May 1, 1983) in South Bend, Ind.

Lineback et al., "Two Forms of Glucoamylase of *Aspergillus niger*", Arch. Biochem. Biophys., 134:539, (1969).

M. J. Bull, Progress in Industrial Microbiology, vol. 15, Elsevier Scientific Publishing Co., Amsterdam, 1979, pp. 117-125.

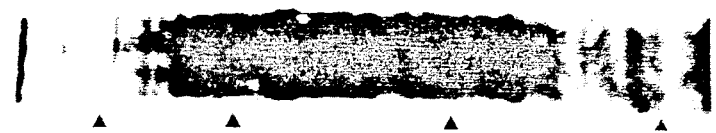

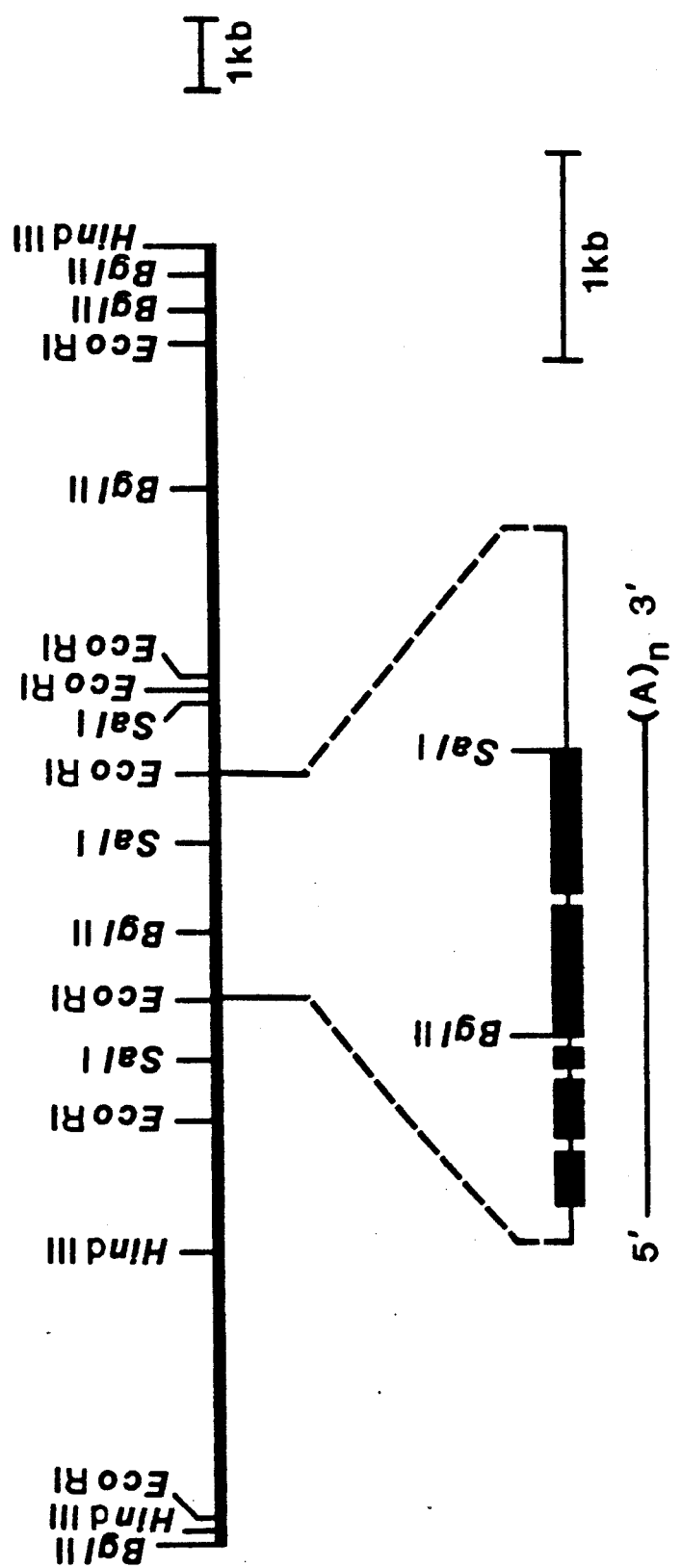

Genomic Clone

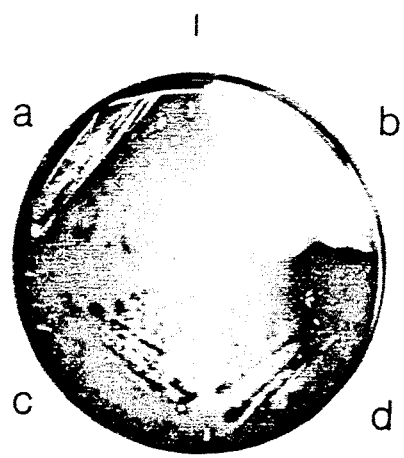
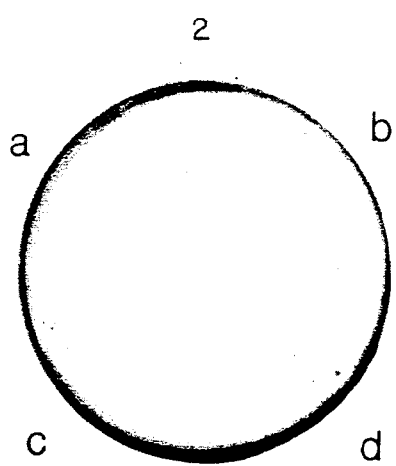
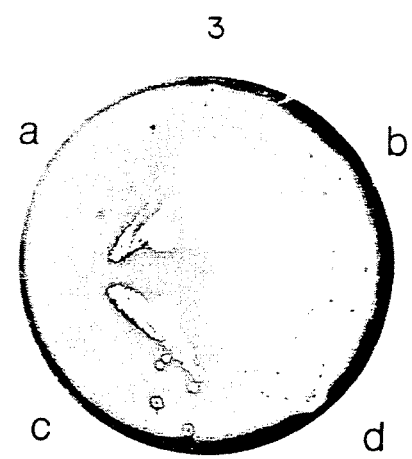
FIG. 9

```
GCG ACC TTG GAT TCA TGG TTG AGC AAC GAA GCG ACC GTG GCT CGT
ACT GCC ATC CTG AAT AAC ATC GGG GCG GAC GGT GCT TGG GTG TCG
GGC GCG GAC TCT GGC ATT GTC GTT GCT AGT CCC AGC ACG GAT AAC
CCG GAC TAC TTC TAC ACC TGG ACT CGC GAC TCT GGT CTC GTC CTC
AAG ACC CTC GTC GAT CTC TTC CGA AAT GGA GAT ACC AGT CTC CTC
TCC ACC ATT GAG AAC TAC ATC TCC GCC CAG GCA ATT GTC CAG GGT
ATC AGT AAC CCC TCT GGT GAT CTG TCC AGC GGC GCT GGT CTC GGT
GAA CCC AAG TTC AAT GTC GAT GAG ACT GCC TAC ACT GGT TCT TGG
GGA CGG CCG CAG CGA GAT GGT CCG GCT CTG AGA GCA ACT GCT ATG
ATC GGC TTC GGG CAG TGG CTG CTT GAC AAT GGC TAC ACC AGC ACC
GCA ACG GAC ATT GTT TGG CCC CTC GTT AGG AAC GAC CTG TCG TAT
GTG GCT CAA TAC TGG AAC CAG ACA GGA TAT GAT CTC TGG GAA GAA
GTC AAT GGC TCG TCT TTC TTT ACG ATT GCT GTG CAA CAC CGC GCC
CTT GTC GAA GGT AGT GCC TTC GCG ACG GCC GTC GGC TCG TCC TGC
TCC TGG TGT GAT TCT CAG GCA CCC GAA ATT CTC TGC TAC CTG CAG
TCC TTC TGG ACC GGC AGC TTC ATT CTG GCC AAC TTC GAT AGC AGC
CGT TCC GGC AAG GAC GCA AAC ACC CTC CTG GGA AGC ATC CAC ACC
TTT GAT CCT GAG GCC GCA TGC GAC GAC TCC ACC TTC AGC CCC TGC
TCC CCG CGC GCG CTC GCC AAC CAC AAG GAG GTT GTA GAC TCT TTC
CGC TCA ATC TAT ACC CTC AAC GAT GGT CTC AGT GAC AGC GAG GCT
GTT GCG GTG GGT CGG TAC CCT GAG GAC ACG TAC TAC AAC GGC AAC
```

FIG.13-1

```
CCG TGG TTC CTG TGC ACC TTG GCT GCC GCA GAG CAG TTG TAC GAT
GCT CTA TAC CAG TGG GAC AAG CAG GGG TCG TTG GAG GTC ACA GAT
GTG TCG CTG GAC TTC TTC AAG GCA CTG TAC AGC GAT GCT GCT ACT
GGC ACC TAC TCT TCG TCC AGT TCG ACT TAT AGT AGC ATT GTA GAT
GCC GTG AAG ACT TTC GCC GAT GGC TTC GTC TCT ATT GTG GAA ACT
CAC GCC GCA AGC AAC GGC TCC ATG TCC GAG CAA TAC GAC AAG TCT
GAT GGC GAG CAG CTT TCC GCT CGC GAC CTG ACC TGG TCT TAT GCT
GCT CTG CTG ACC GCC AAC AAC CGT CGT AAC TCC GTC GTG CCT GCT
TCT TGG GGC GAG ACC TCT GCC AGC AGC GTG CCC GGC ACC TGT GCG
GCC ACA TCT GCC ATT GGT ACC TAC AGC AGT GTG ACT GTC ACC TCG
TGG CCG AGT ATC GTG GCT ACT GGC GGC ACC ACT ACG ACG GCT ACC
CCC ACT GGA TCC GGC AGC GTG ACC TCG ACC AGC AAG ACC ACC GCG
ACT GCT AGC AAG ACC AGC ACC AGT ACG TCA TCA ACC TCC TGT ACC
ACT CCC ACC GCC GTG GCT GTG ACT TTC GAT CTG ACA GCT ACC ACC
ACC TAC GGC GAG AAC ATC TAC CTG GTC GGA TCG ATC TCT CAG CTG
GGT GAC TGG GAA ACC AGC GAC GGC ATA GCT CTG AGT GCT GAC AAG
TAC ACT TCC AGC GAC CCG CTC TGG TAT GTC ACT GTG ACT CTG CCG
GCT GGT GAG TCG TTT GAG TAC AAG TTT ATC CGC ATT GAG AGC GAT
GAC TCC GTG GAG TGG GAG AGT GAT CCC AAC CGA GAA TAC ACC GTT
CCT CAG GCG TGC GGA ACG TCG ACC GCG ACG GTG ACT GAC ACC TGG
CGG
```

FIG. 13-2

```
CCACTAAATCCGATCATTGATCCACCGCCCACGAGGGCGTCTTTGCTTTTTGCGCGGCGT 3024
CCAGGTTCAACTCTCTCTGCAGCTCCAGTCCAACGCTGACTGACTAGTTTACCTACTGGT
CTGATCGGCTCCATCAGAGCTATGGCGTTATCCCGTGCCGTTGCTGCGCAATCGCTATCT 3144
TGATCGCAACCTTGAACTCACTCTTGTTTTAATAGTGATCTTGGTGACGGAGTGTCGGTG
AGTGACAACCAACATCGTGCAAGGGAGATTGATACGGAATTGTCGCTCCCATCATGATGT 3264
TCTTGCCGGCTTTGTTGGCCCTATTCGTGGGATCGATGCCCTCCTGTGCAGCAGCAGGTA
CTGCTGGATGAGGAGCCATCGGTCTCTGCACGCAAACCCAACTTCCTCTTCATTCTCACG 3384
GATGATCAGGATCTCCGGATGAATTC
```

FIG. 12-4

```
CCTGCTTCTTGGGGCGAGACCTCTGCCAGCAGCGTGCCCGGCACCTGTGCGGCCACATCT
ProAlaSerTrpGlyGluThrSerAlaSerSerValProGlyThrCysAlaAlaThrSer

GCCATTGGTACCTACAGCAGTGTGACTGTCACCTCGTGGCCGAGTATCGTGGCTACTGGC   1944
AlaIleGlyThrTyrSerSerValThrValThrSerTrpProSerIleValAlaThrGly    473

GGCACCACTACGACGGCTACCCCCACTGGATCCGGCAGCGTGACCTCGACCAGCAAGACC
GlyThrThrThrThrAlaThrProThrGlySerGlySerValThrSerThrSerLysThr

ACCGCGACTGCTAGCAAGACCAGCACCAGTACGTCATCAACCTCCTGTACCACTCCCACC   2064
ThrAlaThrAlaSerLysThrSerThrSerThrSerSerThrSerCysThrThrProThr    513

GCCGTGGCTGTGACTTTCGATCTGACAGCTACCACCACCTACGGCGAGAACATCTACCTG
AlaValAlaValThrPheAspLeuThrAlaThrThrThrTyrGlyGluAsnIleTyrLeu

GTCGGATCGATCTCTCAGCTGGGTGACTGGGAAACCAGCGACGGCATAGCTCTGAGTGCT   2134
ValGlySerIleSerGlnLeuGlyAspTrpGluThrSerAspGlyIleAlaLeuSerAla    553

GACAAGTACACTTCCAGCGACCCGCTCTGGTATGTCACTGTGACTCTGCCGGCTGGTGAG
AspLysTyrThrSerSerAspProLeuTrpTyrValThrValThrLeuProAlaGlyGlu

TCGTTTGAGTACAAGTTTATCCGCATTGAGAGCGATGACTCCGTGGAGTGGGAGAGTGAT   2304
SerPheGluTyrLysPheIleArgIleGluSerAspAspSerValGluTrpGluSerAsp    593

CCCAACCGAGAATACACCGTTCCTCAGGCGTGCGGAACGTCGACCGCGACGGTGACTGAC
ProAsnArgGluTyrThrValProGlnAlaCysGlyThrSerThrAlaThrValThrAsp

ACCTGGCGGTAGACAATCAATCCATTTCGCTATAGTTAAAGGATGGGGATGAGGGCAATT   2424
ThrTrpArg                                                       616

GGTTATATGATCATGTATGTAGTGGGTGTGCATAATAGTAGTGAAATGGAAGCCAAGTCA

TGTGATTGTAATCGACCGACGGAATTGAGGATATCCGGAAATACAGACACCGTGAAAGCC   2544

ATGGTCTTTCCTTCGTGTAGAAGACCAGACAGACAGTCCCTGATTTACCCTGCACAAAGC

ACTAGAAAATTAGCATTCCATCCTTCTCTGCTTGCTCTGCTGATATCACTGTCATTCAAT   2664

GCATAGCCATGAGCTCATCTTAGATCCAAGCACGTAATTCCATAGCCGAGGTCCACAGTG

GAGCAGCAACATTCCCCATCATTGCTTTCCCCAGGGGCCTCCCAACGACTAAATCAAGAG   2784

TATATCTCTACCGTCCAATAGATCGTCTTCGCTTCAAAATCTTTGACAATTCCAAGAGGG

TCCCCATCCATCAAACCCAGTTCAATAATAGCCGAGATGCATGGTGGAGTCAATTAGGCA   2904

GTATTGCTGGAATGTCGGGGCCAGTTCCGGGTGGTCATTGGCCGCCTGTGATGCCATCTG
```

FIG. 12-3

```
AGGATATGgtgtgtttgttttattttaaatttccaaagatgcgccagcagagctaacccg      994
rGlyTyr                                                           175 cgatcgcagATCTCTGGGAAGAAGTCAATGGCTCGTCTTTCTTTACGATTGCTGTGCAAC
         AspLeuTrpGluGluValAsnGlySerSerPhePheThrIleAlaValGlnH ACCGCGCCCTTGTCGAAGGTAGTGCCTTCGCGACGGCCGTCGGCTCGTCCTGCTCCTGGT     1104
isArgAlaLeuValGluGlySerAlaPheAlaThrAlaValGlySerSerCysSerTrpC      212

GTGATTCTCAGGCACCCGAAATTCTCTGCTACCTGCAGTCCTTCTGGACCGGCAGCTTCA
ysAspSerGlnAlaProGluIleLeuCysTyrLeuGlnSerPheTrpThrGlySerPheI

TTCTGGCCAACTTCGATAGCAGCCGTTCCGGCAAGGACGCAAACACCCTCCTGGGAAGCA     1224
leLeuAlaAsnPheAspSerSerArgSerGlyLysAspAlaAsnThrLeuLeuGlySerI      252

TCCACACCTTTGATCCTGAGGCCGCATGCGACGACTCCACCTTCCAGCCCTGCTCCCCGC
leHisThrPheAspProGluAlaAlaCysAspAspSerThrPheGlnProCysSerProA

GCGCGCTCGCCAACCACAAGGAGGTTGTAGACTCTTTCCGCTCAATCTATACCCTCAACG     1344
rgAlaLeuAlaAsnHisLysGluValValAspSerPheArgSerIleTyrThrLeuAsnA      292

ATGGTCTCAGTGACAGCGAGGCTGTTGCGGTGGGTCGGTACCCTGAGGACACGTACTACA
spGlyLeuSerAspSerGluAlaValAlaValGlyArgTyrProGluAspThrTyrTyrA

ACGGCAACCCGTGGTTCCTGTGCACCTTGGCTGCCGCAGAGCAGTTGTACGATGCTCTAT     1464
snGlyAsnProTrpPheLeuCysThrLeuAlaAlaAlaGluGlnLeuTyrAspAlaLeuT      332

ACCAGTGGGACAAGCAGGGGTCGTTGGAGGTCACAGATGTGTCGCTGGACTTCTTCAAGG
yrGlnTrpAspLysGlnGlySerLeuGluValThrAspValSerLeuAspPhePheLysA

CACTGTACAGCGATGCTGCTACTGGCACCTACTCTTCGTCCAGTTCGACTTATAGTAGCA     1584
laLeuTyrSerAspAlaAlaThrGlyThrTyrSerSerSerSerThrTyrSerSerI       372

TTGTAGATGCCGTGAAGACTTTCGCCGATGGCTTCGTCTCTATTGTGtaagtctacgct
leValAspAlaValLysThrPheAlaAspGlyPheValSerIleVal agacaagcgctcatgttgacagagggtgcgtactaacagaagtagGAAACTCACGCCGCA     1704
                                             GluThrHisAlaAla     393

AGCAACGGCTCCATGTCCGAGCAATACGACAAGTCTGATGGCGAGCAGCTTTCCGCTCGC
SerAsnGlySerMetSerGluGlnTyrAspLysSerAspGlyGluGlnLeuSerAlaArg

GACCTGACCTGGTCTTATGCTGCTCTGCTGACCGCCAACAACCGTCGTAACTCCGTCGTG     1824
AspLeuThrTrpSerTyrAlaAlaLeuLeuThrAlaAsnAsnArgArgAsnSerValVal     433
```

FIG.12-2

```
                                              GAATTCAAGCTAGATGCTAAGCGA    24
TATTGCATGGCAATATGTGTTGATGCATGTGCTTCTTCCTTCAGCTTCCCCTCGTGCAGA
TGAGGTTTGGCTATAAATTGAAGTGGTTGGTCGGGGTTCCGTGAGGGGCTGAAGTGCTTC           144
CTCCCTTTTAGACGCAACTGAGAGCCTGAGCTTCATCCCCAGCATCATTACACCTCAGCA

ATGTCGTTCCGATCTCTACTCGCCCTGAGCGGCCTCGTCTGCACAGGGTTGGCAAATGTG          264
MetSerPheArgSerLeuLeuAlaLeuSerGlyLeuValCysThrGlyLeuAlaAsnVal          -20
ATTTCCAAGCGCGCGACCTTGGATTCATGGTTGAGCAACGAAGCGACCGTGGCTCGTACT
IleSerLysArgAlaThrLeuAspSerTrpLeuSerAsnGluAlaThrValAlaArgThr
GCCATCCTGAATAACATCGGGGCGGACGGTGCTTGGGTGTCGGGCGCGGACTCTGGCATT          384
AlaIleLeuAsnAsnIleGlyAlaAspGlyAlaTrpValSerGlyAlaAspSerGlyIle           36
GTCGTTGCTAGTCCCAGCACGGATAACCCGGACTgtatgtttcgagctcagatttagtat
ValValAlaSerProSerThrAspAsnProAsp
gagtgtgtcattgattgattgatgctgactggcgtgtcgtttgttgtagACTTCTACACC          504
                                                 TyrPheTyrThr           51
TGGACTCGCGACTCTGGTCTCGTCCTCAAGACCCTCGTCGATCTCTTCCGAAATGGAGAT
TrpThrArgAspSerGlyLeuValLeuLysThrLeuValAspLeuPheArgAsnGlyAsp
ACCAGTCTCCTCTCCACCATTGAGAACTACATCTCCGCCCAGGCAATTGTCCAGGGTATC         624
ThrSerLeuLeuSerThrIleGluAsnTyrIleSerAlaGlnAlaIleValGlnGlyIle           91
AGTAACCCCTCTGGTGATCTGTCCAGCGGCGCTGGTCTCGGTGAACCCAAGTTCAATGTC
SerAsnProSerGlyAspLeuSerSerGlyAlaGlyLeuGlyGluProLysPheAsnVal
GATGAGACTGCCTACACTGGTTCTTGGGGACGGCCGCAGCGAGATGGTCCGGCTCTGAGA         744
AspGluThrAlaTyrThrGlySerTrpGlyArgProGlnArgAspGlyProAlaLeuArg          131
GCAACTGCTATGATCGGCTTCGGGCAGTGGCTGCTTgtatgttctccaccccttgcgtc
AlaThrAlaMetIleGlyPheGlyGlnTrpLeuLeu
tgatctgtgacatatgtagctgactggtcagGACAATGGCTACACCAGCACCGCAACGGA         864
                               AspAsnGlyTyrThrSerThrAlaThrAs          153
CATTGTTTGGCCCCTCGTTAGGAACGACCTGTCGTATGTGGCTCAATACTGGAACCAGAC
pIleValTrpProLeuValArgAsnAspLeuSerTyrValAlaGlnTyrTrpAsnGlnTh
```

FIG.12-1

DNA EXPRESSION VECTOR AND USE THEREOF

CROSS-REFERENCE TO RELATED APPLICATION

This application is a continuation of copending U.S. application Ser. No. 563,941, filed Dec. 20, 1983, now abandoned, which is related to copending U.S. application Ser. No. 461,920 filed Jan. 28, 1983, entitled "Glucoamylase cDNA."

REFERENCES

The following publications are referred to by corresponding number in this application:
1. Lineback, et al., *Cereal Chemistry*, 49:283 (1972).
1a. Svensson, et al., *Carlsberg Res. Commun.*, 47:55 (1982).
1b. Svensson, et al., Abstract IV-27, XIth International Carbohydrate Symposium, Vancouver, British Columbia, Aug., 1982.
1c. Botstein, et al., in *The Molecular Biology of the Yeast Saccharomyces-Metabolism and Gene Expression*, ed. by Strathern, et al. (New York: Cold Spring Harbor Laboratory, 1982), p.607ff.
1d. Struhl, *Nature*, 305:391 (1983).
1e. European Pat. Application 81303155.6 (Publication 45573 dated Feb. 10, 1982) to Stanford University.
2. Chirgwin, et al., *Biochem.*, 18:5294 (1979).
3. Sehgal, *Methods in Enzymology*, 79:111 (1981), at p. 117.
4. Pelham, et al., *Eur. J. Biochem.*, 67:247 (1976).
5. Maniatis, et al., Molecular Cloning: A Laboratory Manual, publ., Cold Spring Harbor, N.Y. (1982), pp. 344-349.
6. Ivarie, et al., *Anal. Biochem.*, 97:24 (1979).
7. Chang, et al., *Nature*, 275:617 (1978).
8. Doel, et al., *Nucleic Acids Res.*, 4:3701 (1977).
9. Southern, *J. Mol. Biol.*, 98:503 (1975).
10. Sanger, et al., *Proc. Nat. Acad. Sci. USA*, 74:5463 (1977).
11. Messing, et al., *Nucleic Acid Res.*, 9:309 (1981).
12. Maxam, et al., *Proc. Nat. Acad. Sci. USA*, 74:560 (1977).
13. Mount, *Nucl. Acids Res.*, 10:459 (1982).
14. Langford, et al., *Proc, Natl. Acad, Sci. USA*, 80:1496 (1983).
15. Langford, et al., *Cell*, 33:519 (1983).
16. Holland, et al., *J.Biol. Chem.*, 256:1385 (1981).
16a. Sutcliffe, *Cold Spring Harbor Symposium on Quantitative Biology*, 43: 77 (1978).
16b. Broach, et al., *Gene*, 8: 121 (1979).
16c. Beach, et al., *Nature*, 290: 140 (1981).
17a. Erlich, et al., *J. Biol. Chem.* 254:12,240 (1979).
17b. Erlich, et al., *Inf. and Imm.*, 41:683 (1983).
18. Dewald, et al., in *Methods in Enzymology*, Vol. XXXII, Biomembranes, Part B, ed. by Fleischer et al. (New York: Academic Press, 1974), p. 87-88.

BACKGROUND OF THE INVENTION

The present invention relates to a glucoamylase gene, to a method for isolating such gene, and to a host which is transformed by an expression vector of said gene and produces glucoamylase.

The techniques of genetic engineering have been successfully applied to the pharmaceutical industry, resulting in a number of novel products. Increasingly, it has become apparent that the same technologies can be applied on a larger scale to the production of enzymes of value to other industries. The benefits of achieving commercially useful processes through genetic engineering are expected to include: (1) cost savings in enzyme production, (2), production of enzymes in organisms generally recognized as safe which are more suitable for food products, and (3) specific genetic modifications at the DNA level to improve enzyme properties such as thermal stability and other performance characteristics.

One important industrial application of genetic engineering involves improving the ability of industrial yeast strains to degrade complex carbohydrate substrates such as starch. Yeasts such as *Saccharomyces cerevisiae* which are suitable for alcoholic fermentation do not produce an enzyme capable of hydrolyzing starch to utilizable substrates. Currently, starch used as a food source in alcoholic fermentation must be saccharified, either chemically or enzymatically, in a separate process to produce utilizable substrates for the fermenting yeast.

It would thus be desirable to construct, by genetic recombination methods, a fermentation yeast such as *S. cerevisiae* which itself has the capacity to synthesize one or more enzymes capable of breaking down starchy to utilizable substrates. European Pat. Appln. 0,034,470 discloses preparing recombinant DNA containing an amylase encoding gene by cleaving a bacterial donor microorganism to obtain DNA and inserting those fragments in a vector. The amylase enzymes produces from the DNA which are used to hydrolyze starch are preferably alpha-amylase, beta-amylase or a pullulanase.

SUMMARY OF THE INVENTION

Accordingly, in one aspect, the present invention is concerned with constructing a fermentation yeast which contains, in recombinant form, a gene coding for a glucoamylase which is active in hydrolyzing starch at both alpha 1-4 alpha 1-6 linkages to generate glucose.

The present invention generally concerns the construction of a glucoamylase gene which can be introduced in recombinant form into a foreign host including but not limited to yeast or bacteria. Such hosts may also include plant or animal cells.

According to one aspect of the invention, there is provided a modified DNA sequence coding for fungal glucoamylase protein or its single or multiple base substitutions, deletions, insertions or inversions, wherein said DNA sequence is derived from natural, synthetic or semi-synthetic sources and is capable, when correctly combined with a cleaved expression vector, of expressing a non-native protein having glucoamylase enzyme activity upon transformation by the vector of a microorganism host. Most preferably the expression vector is the plasmid pACl described further hereinbelow which has been cleaved at its HindIII site so that the sequence can be inserted at that site.

According to another aspect of the invention, it has been discovered that *Aspergillus awamori* cells, when grown under conditions which induce glucoamylase, contain a relatively high concentration of approximately 2.2 kilobase poly A RNA which is not detected in cells grown under noninducing conditions. The induced poly A RNA (mRNA) is capable of directing the synthesis, in a cell-free protein synthesizing system, of an unglycosylated polypeptide which has a molecular weight of between about 70,000 and 74,000 daltons. The polypeptide produced is immunologically reactive with antibodies prepared against *A. awamori* glucoamylase.

A radioactively labeled cDNA copy of the induced poly A RNA is produced which is used in hybridization studies to identify *A. awamori* genomic DNA fragments containing portions of the glucoamylase gene. The hybridization studies suggest that *A. awamori* contains a single glucoamylase gene.

Similarly, the cDNA is used to identify phage or plasmid vectors containing such genomic DNA fragments in recombinant form. The identified cloning vectors may be used in determining gene polynucleotide sequences and sequence homology with the cDNA.

When a HindIII fragment containing the *A. awamori* glucoamylase gene is inserted into yeast, neither transcription nor translation in these heterologous hosts is detected.

The invention also provides for recombinant DNA expression vectors containing the DNA sequence. The vector is preferably one which is compatible with a selected foreign microorganism host, and permits expression of the gene in the host. The exogenous gene which is expressed may be genomic DNA, synthetic DNA or a cDNA obtained from a mRNA by use of reverse transcriptase.

A novel method for producing a glucoamylase gene containing the appropriate DNA sequence generally includes producing genomic digest fragments, providing a glucoamylase probe, using the probe to identify genomic digest fragments containing glucoamylase gene regions, molecularly cloning the identified genomic digest fragments, molecularly cloning partial cDNA, sequencing the genomic and cDNA clones, comparing the sequenced glucoamylase gene regions with all or a portion of the amino acid sequence of the mature glucoamylase enzyme to determine the existence and location of all the introns and exons in the genomic clones, and constructing a gene whose codon sequence is substantially identical to that of the genomic glucoamylase gene when the sequences comprising the introns are deleted.

In a preferred embodiment of the method, the glucoamylase probe is provided by selecting a fungal source capable of producing a level of glucoamylase, when grown on starch, which is at least about ten times that produced by the fungal species when grown on xylose or glycerol in the absence of starch, culturing cells of the selected fungus under conditions which induce secretion of glucoamylase into the culture medium, obtaining mRNA from the cultured cells, fractionating the mRNA obtained according to size, selecting an mRNA which is detectable as having a relatively high concentration with respect to the equivalent-sized mRNA produced by cells of the selected fungal species cultured under conditions which do not induce secretion of glucoamylase into the culture medium, and copying the selected mRNA to produce the glucoamylase probe.

In yet another embodiment of the invention is provided a host organism transformed with a DNA expression vector comprising a promoter fragment that functions in that host and a DNA segment having a modified DNA sequence coding for fungal glucoamylase protein, the DNA segment being in an orientation with the promoter fragment such that in the host it is expressed to produce a non-native glucoamylase protein.

The gene herein, when expressed in a host organism transformed by an expression vector comprising the gene, produces an enzyme having glucoamylase activity. Preferably the glucoamylase enzyme is produced as a preprotein with a signal sequence at its $NH_2$-terminus which is processed by the host organism during secretion.

In another embodiment, the invention relates to a process for producing glucose by saccharification of starch using a recombinant glucoamylase gene.

In another embodiment, the invention relates to a process for producing ethanol by simultaneous saccharification and fermentation which comprises growing, on a nonfermentable carbon source which is a substrate for glucoamylase enzyme, a host organism transformed by the DNA expression vector described above. The carbon source is preferably starch, soluble starch, maltose or isomaltose.

In yet another embodiment, the invention relates to a process for secreting any proteinaceous material extracellularly which comprises growing a host organism in a culture medium, which host is transformed by a DNA expression vector comprising a promoter fragment which function in the host organism, a signal sequence having substantially the following amino acid sequence:

MET SER PHE ARG SER LEU LEU ALA LEU SER GLY LEU VAL CYS THR GLY LEU ALA ASN VAL ILE SER LYS ARG and a DNA segment which codes for the proteinaceous material.

Preferably, the proteinaceous material is a protein which is normally secreted and most preferably it is glucoamylase. The vector may or may not contain a DNA segment which functions as an origin of replication, a selectable marker or a transcription terminator segment.

In the invention herein, the glucoamylase enzyme obtained when the heterologous gene is expressed in yeast is found to be glycosylated. In addition, a significant portion (e.g., greater than 90%) of the glucoamylase is secreted in the media. Also, when the N-terminus of the non-native glucoamylase protein secreted in the media (having a purity of greater than 85%) was sequenced, the first 29 amino acids were found to be identical to the mature glucoamylase protein secreted by *Aspergillus*. The apparent molecular weight as determined by SDS polyacrylamide gel electrophoresis of the glucoamylase protein obtained herein is similar to that observed for the mature processed and glycosylated form of the native glucoamylase secreted by *Aspergillus*. Further, the carboxy terminal amino acid is identical to that of the arge molecular weight form of glucoamylase produced by Aspergillus.

BRIEF DESCRIPTION OF THE DRAWINGS

FIG. 1 represents gel electrophoretic patterns showing in vitro translation of *A. awamori* mRNA from cells grown in medium containing xylose or starch as carbon source. Translation products were immunoprecipitated using rabbit anti-glucoamylase antibody (lane 1, xylose-grown cells; lane 3, starch-grown cells) or normal rabbit antibody (lane 2, xylose-grown cells; lane 4, starch-grown cells).

In FIG. 2A, poly A-containing mRNA from cells grown in medium containing starch (lane 1) or xylose (lane 2) was analyzed by MeHgOH-agarose gel electrophoresis. Human and *E. coli* ribosomal RNAs provide molecular weight markers. The *A. awamori* ribosomal RNAs are indicated as '28S' and '18S'. The major 'induced2 mRNA (arrow) was isolated from the gel and used to direct in vitro translation. In FIG. 2B, total translation products of reactions containing no exogenous mRNA (lane 1) or the isolated major 'induced' mRNA (lane 2) are shown. Immunoprecipitation of protein products in lane 2, using rabbit anti-glucoamylase antibody, is shown in lane 3.

FIG. 3 shows a restriction endonuclease map of *A. awamori* genome surrounding the glucoamylase gene. The entire structural gene is contained within the 3.4 kilobase EcoRI fragment isolated from the Charon 4A library. The protein-encoding regions of the glucoamylase gene are indicated as solid boxes and the arrow indicates the direction and extent of transcription.

FIG. 4 shows gel electrophoretic patterns where pGAR1 is used to hybridize to, and select, glucoamylase mRNA. Total *A. awamori* mRNA (lane 1) and mRNA isolated by virtue of hybridization to pGARI DNA (lane 2) was translated in vitro and the protein products are displayed. Protein products of lane 2 are immunoprecipitated using rabbit anti-glucoamylase antibody (lane 3) or normal rabbit antibody (lane 4).

FIG. 9 illustrates plate assays for degradation of Baker's starch by various transformed yeast strains. The strains given below were streaked on minimal media containing histidine at 40 mg/1 and 2% w/v Baker's starch. After 12 days incubation at 30° C. the plates were stained with iodine vapors. The starch was stained purple, and the clear zones represent regions in which the starch has been hydrolyzed.

| Plate | Area of Plate | Yeast | Plasmid |
|---|---|---|---|
| 1 | a | C468 | pAC1 |
|   | b | C468 | pGAC9 |
|   | c | C468 | pGC21 |
|   | d | C468 | pGC21 |
| 2 | a | C468 | pAC1 |
|   | b | C468 | pGAC9 |
|   | c | C468 | pGAC9 |
|   | d | C468 | pGAC9 |
| 3 | a | H18 | pAC1 |
|   | b | H18 | pGAC9 |

-continued

| Plate | Area of Plate | Yeast | Plasmid |
|---|---|---|---|
|   | c | C303* |  |
|   | d | H18 | pGAC9 |

*C303 strain is *S. diastaticus*.

Figure 10:
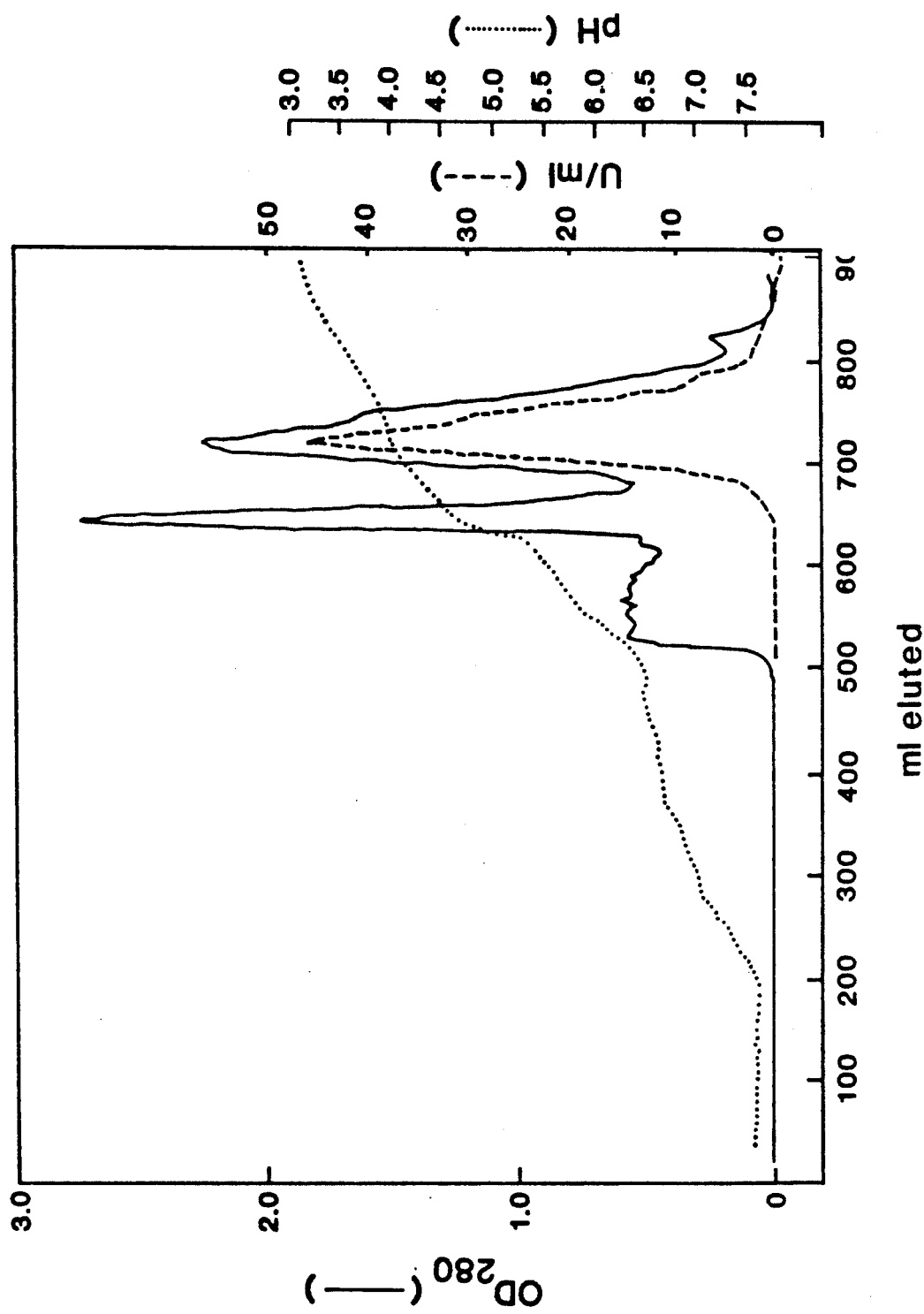

FIG. 10 shows DEAE-Sepharose chromatography of glucoamylase produced by the recombinant yeast in a 10-liter fermentor.

Figure 11:
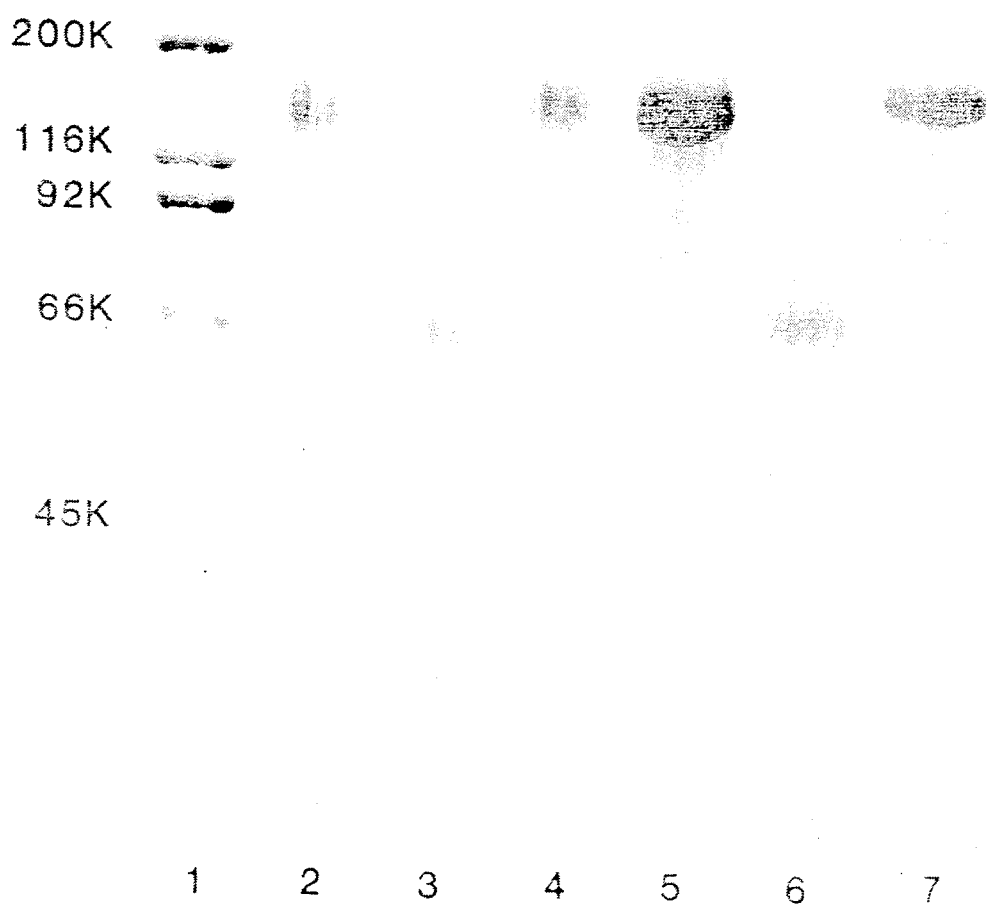

FIG. 11 shows gel electrophoretic patterns of: BioRad High Molecular Weight Protein Standards (lane 1), 25 μg *A. awamori* glucoamylase-1 (lane 2 and 5), 25 μg *A. awamori* glucoamylase-II (lane 3 and 6), and 25 μg recombinant glucoamylase (lane 4 and 7). Lanes 1–4 were stained with Coomassie Blue stain and lanes 5–7 with Periodic Acid Schiff's stain.

FIG. 12 shows the sequence of the EcoRI fragment in pGAR1 which contains the *A. Awamori* glucoamylase gene, the introns, and the putative amino acids encode in the exons.

FIG. 13 shows the nucleotide sequence of cDNA in pGAC9, which encodes glucoamylase.

DETAILED DESCRIPTION OF THE PREFERRED EMBODIMENTS

The following terms used in the description are defined below:

"DNA sequence" refers to a linear array of nucleotides connected on to the other by phosphodiester bonds between the 3' and 5' carbons of adjacent pentoses.

"Modified DNA sequence" refers to a DNA sequence which is altered from the native glucoamylase DNA sequence such as by removing the introns from or modifying the introns of the native sequence. The examples illustrate sequences which are free of introns. Sequences substantially free of introns means greater than about 80% free.

"Glucoamylase enzyme activity" refers to the amount by which the enzyme in contact with an aqueous slurry of starch or starch hydrolysate degrades starch to glucose molecules.

"Single or multiple base substitutions and deletions, insertions and inversions" of the basic modified DNA sequence refer to degeneracy in the DNA sequence where the codons may be mutated or the deoxyribonucleotides may be derivatized to contain different bases or other elements, but the DNA sequence thus altered is still capable, on transformation in a host, of expressing glucoamylase protein.

"Fungal glucoamylase protein" refers to protein which is not derived from a bacterial source, but rather from a fungal source such as a strain from the genus Aspergillus. Thus, a modified DNA sequence coding for fungal glucoamylase protein signifies that the DNA is not derived from a bacterial donor microorganism.

"Non-native glucoamylase protein" refers to glucoamylase protein not produced naturally or natively by the microorganism used as the host.

"Nonfermentable carbon source which is a substrate for glucoamylase" refers to substrates for the glucoamylase enzyme which the host cannot ferment, such as starch, maltose, isomaltose and other starch derived oligosaccharides. Cellulose is not a substrate for glucoamylase and thus is not contemplated in this definition.

The present invention relates to a modified DNA sequence and an expression vector into which the gene has been introduced by recombinant DNA techniques, which, when transformed in a host organism, expresses glucoamylase. The modified DNA sequence may be derived from a natural, synthetic or semi-synthetic source. Preferably it is derived from a selected native fungal source which produces an induced level of glucoamylase which is at least about ten times its uninduced level. The induced level is that which is produced by the fungal species when grown on starch as a sole or primary carbon source, and the uninduced level, that observed when the fungal species is grown on glycerol or xylose.

The selected fungus for producing glucoamylase is suitably cultured under glucoamylase-induction conditions and a poly A RNA fraction from the cultured cells is isolated and size fractionated to reveal a glucoamylase mRNA present in a detectably higher concentration than in mRNA from uninduced cells. A glucoamylase cDNA is produced by copying the mRNA, using a reverse transcriptase.

A preferred DNA sequence contemplated in the present invention is the sequence coding for the fungal glucoamylase (amyloglucosidase) from filamentous fungi, preferably a species of the class Ascomycetes, preferably the filamentous Ascomycetes, more preferably from an Aspergillus species, and most preferably Aspergillus awamori. The native enzyme obtained from these sources is active in breaking down high molecular weight starch, and is able to hydrolyze alpha 1-6 branch linkages as well as alpha 1-4 chain linkages. Relatively high levels of the enzyme are produced and secreted in A. awamori cultures grown on starch and a variety of 6-carbon sugars, such as glucose.

Although the invention will be described with particular reference to A. awamori as a source of the DNA sequence, it is recognized that the invention applies to other fungal species which have an inducible glucoamylase, preferably species of the Aspergillus genus. In particular, A. awamori glucoamylase appears to be similar, if not identical, to Aspergillus niger glucoamylase, as will be seen below.

The fungal species A. awamori was selected for detailed study. This fungal species, when grown on starch as a sole or primary carbon source, produces an amount of glucoamylase in the culture medium, based on measurable enzyme activity per cell dry weight, which is about 200 times that of cells grown on xylose or glycerol.

A. awamori, when grown on starch, produces and secretes at least two physically distinguishable glucoamylase enzymes. One of these enzymes, referred to as glucoamylase-I, has a molecular weight of about 74,900 daltons, as reported in Reference 1, and is glycosylated at some or all of the peptide serine and threonine residues. A second enzyme, glucoamylase-II, has a molecular weight of about 54,300 daltons, as reported in Reference 1, and is also glycosylated. It is noted that the sizes of the glycosylated glucoamylase protein given herein are only approximate, because glycoproteins are difficult to characterize precisely.

Several lines of evidence suggest that the two A. awamori glucoamylase enzymes are derived from a common polypeptide. Antibodies prepared against each enzyme form react immunospecifically with the other form, as will be seen below. The two enzymes have identical amino acid sequences in N-terminal fragments containing about 30 amino acids each. Further, these N-terminal sequences are identical to those in glucoamylase I and II forms from Aspergillus niger, and the two A. niger glucoamylase forms appear to be derived from a common polypeptide, as reported in Reference 1a. Experiments performed in support of the present application, discussed below, indicate that a single A. awamori glucoamylase gene codes for a single glucoamylase polypeptide precursor, which is very similar, if not identical, to that produced by A. niger.

According to one aspect of the invention, it has been discovered that cells of a selected fungal species, when grown under conditions which induce the secretion of glucoamylase into the culture medium, contain poly A RNA which is essentially undetectable in cells grown under noninducing conditions. The poly A RNA is capable of directing the synthesis, in a cell-free protein synthesizing system, of a polypeptide which is immunologically reactive with antibodies prepared against the glucoamylase from that fungal species.

Because the gene is not expressed in yeast hosts with its intact regulatory elements, it is necessary to delete or modify the introns and to exchange promoters so that the yeast will transcribe the gene, translate the mRNA, and produce an active glucoamylase.

The introns may be removed from the glucoamylase gene either by methods known in the literature for removing introns or by the simpler method described in section B of Example 2 below using specific restriction enzymes in various steps to create fragments which are then ligated together and using site-directed mutagenesis. In the mutagenesis technique the 5'-most intron of the glucoamylase gene is removed using a primer which is homologous to sequences on both sides of the intron and annealing this primer to a single-stranded DNA template of the glucoamylase genomic clone. The primer is then used to prime DNA synthesis of the complementary strand by extension of the primer on an M13 single-stranded phage DNA template. The resulting molecules were double-stranded circular molecules with single-stranded loops containing the intron sequence. When the molecules are transformed into cells, these loops may be excised, thereby removing the intron, but even without excision DNA replication will generate the correct progeny. If the introns are present in the gene, little or no glucoamylase enzyme is produced in a yeast in which the gene is expressed.

After the introns have been removed therefrom, the glucoamylase gene may be inserted by genetic recombination into a DNA expression vector, preferably a plasmid, which may then be used to transform a microorganism host. Suitable microorganisms for this purpose include bacteria such as E. coli, viruses and yeasts. The microorganism host useful in this present invention must contain the appropriate genetic background for transformation thereof, i.e., the expression vector is compatible with the genetic background of the host strain. For example, the host recipient yeast strains C468 and H18, which are haploid S. cerevisiae laboratory strains employed in the following examples illustrating yeast hosts, are deficient in β-isopropylmalate dehydrogenase activity and therefore are complemented to leucine prototrophy by inserting into the expression vector the selectable marker β-isopropylmalate dehydrogenase (LEU 2). While the expression vector may by itself be capable of phenotypic selection by containing a selectable marker, it need not be so capable because the host can be screened or selected for the glucoamylase gene.

The preferred bacterial host herein is *E coli.* The preferred yeast host strain herein is from a species of the genus *Saccharomyces,* preferably *S. cerevisiae, S. uvarum, S. carlsbergensis,* or mixtures or mutants thereof, more preferably a *S. cerevisiae* strain, and most preferably yeast strain C468 described further hereinbelow.

DNA expression or DNA transfer vectors suitable for transfer and replication have been described, e.g., in References 1c and 1d. Many of the yeast vectors in present use are derived from *E. coli* vectors such as pBR322. These references, 1c and 1d in particular, describe integrative transformation where the microorganism host is transformed with vectors with no origin of replication that integrate into the host chromosome and are maintained and replicated as part of that chromosome. In another embodiment of this invention the host may be transformed by autonomous replication where the vectors contain DNA segments which serve as origins of DNA replication in the host cell. Vectors containing autonomously replicating segments are also described in Reference 1e. Preferably the DNA segment capable of functioning as an origin of replication is from yeast. Two types of such origins of replication from yeast are: one derived from a naturally occurring yeast plasmid, commonly referred to as the 2 micron circle, which confers the ability to replicate independently of yeast chromosomal DNA, and one derived from the yeast chromosomal replication origin containing a replication origin sequence termed ars (autonomous replication sequence), which also provides autonomous replication capability.

The expression vector of this invention necessarily contains a promoter fragment which functions in microorganisms, i.e., the host being employed, as well as the modified DNA sequence coding for the fungal glucoamylase protein. The protein-encoding segment must be so oriented with the promoter fragment that in a microorganism host it is expressed to produce non-native glucoamylase. For bacteria such as *E. coli* a trp promoter is preferred. For yeast, a yeast promoter fragment is preferred. Among possible yeast promoter fragments for purposes herein are included, e.g., alcohol dehydrogenase (ADH-1), 3-phosphoglycerokinase (PGK), pyruvate kinase (PYK), triose phosphate isomerase (TPI), beta-isopropylmalate dehydrogenase (LEU2), glyceraldehyde 3-phosphate dehydrogenase (TDH), enolase I (EN01), and the like. A preferred promoter fragment for purposes herein is from the enolase I gene.

The expression vector herein also preferably contains a microorganism transcription terminator segment following the segment coding for the protein, in a direction of transcription of the coding segment. Examples of possible transcription segments include the 3' segments of the above-listed genes. A preferred transcription terminator segment is from the enolase I gene.

A preferred host system consists of the *S. cerevisiae* yeast host strain C468 transformed by the plasmid pGAC9. This preferred transformed yeast strain was deposited with the American Type Culture Collection (ATCC), 12301 Parklawn Drive, Rockville, Md. 20852 on Nov. 17, 1983 and assigned ATCC Deposit Number 20,690. Another preferred host system consists of the i *E. coli* host strain MH70 transformed by the plasmid pGC24, which transformant was deposited with the ATCC on Dec. 16, 1983, and assigned ATCC Deposit Number 39,537.

The *A. awamori* glucoamylase signal sequence described below is shown to function in yeast for the efficient processing and secretion of glucoamylase from yeast. This sequence could also be used for the secretion of other proteins from yeast and preferably for the secretion of proteins that are normally secreted by their native host. Examples of such proteins include amylases, cellulases, proteases, interferons, lymphokines, insulin, and hormones.

The following examples serve to exemplify the practice of the invention. They are presented for illustrative purposes only, and should not be construed as limiting the invention in any way. Percentages are by weight unless specified otherwise. All experiments were performed following the NIH (U.S.A.) guidelines for containment.

EXAMPLES

All of the strains employed in the examples which have been deposited in depositories were deposited either with the U.S. Department of Agriculture Agricultural Research Service, National Regional Research Laboratories (NRRL) of Peoria, Ill. 61604 or with the American Type Culture Collection (ATCC) of Rockville, Md. 20852. Each strain deposited with ATCC has the individual ATCC designations indicated in the examples pursuant to a contract between the ATCC and the assignee of this patent application, Cetus Corporation. The contract with ATCC provides for permanent availability of the progeny of these strains to the public on the issuance of the U.S. patent describing and identifying the deposits or the publications or upon the laying open to the public of any. U.S. or foreign patent application, whichever comes first, and for availability of the progeny of these strains to one determined by the U.S. Commissioner of Patents and Trademarks to be entitled thereto according to 35 U.S.C. 122 and the Commissioner's rules pursuant thereto (including 37 CFR 1.14 with particular reference to 886 OG 638). The assignee of the present application has agreed that if any of these strains on deposit should die or be lost or destroyed when cultivated under suitable conditions, it will be promptly replaced on notification with a viable culture of the same strain. The NRRL deposits mentioned in the examples and not designated patent deposits have been freely available to the public prior to the filing date of this application. In the examples all parts and percentages are given by weight and all temperatures in degrees Celsius unless otherwise noted.

EXAMPLE 1

Determination of Nucleotide Sequence of Glucoamylase Gene

Experimentally, *A. awamori* cells were grown on either starch or xylose, as a primary source of carbon. The *A. awamori* cells were obtained from NRRL, Deposit Number 3112, and have been recently redeposited and assigned NRRL Deposit Number 15271. Fungal growth was initiated from a suspension of spores in water. The fungal cells were grown in an agitated culture at 30° C. for 2–5 days in a standard growth medium (1% w/v yeast extract, 0.01 M ammonium sulfate, 0.025 M potassium phosphate buffer, pH 7.0) together with 5% w/v of either starch or xylose. As noted above, cells grown on starch produced an amount of glucoamylase in the culture medium, based on measurable enzyme activity per cell dry weight, that was about 200 times that of cells grown on xylose.

Total cellular RNA was isolated from the fungal cultures by a guanidium thiocyanate/CsCl procedure essentially as described in Reference 2. Briefly, mycelia were wrung dry in cheese-cloth, frozen in liquid nitrogen, and ground to a powder in a mortar and pestle in liquid nitrogen. The cell powder was homogenized in a guanidium thiocyanate solution containing 10 mM adenosine: $VOSO_4$ complex. Following centrifugation to pellet cellular debris, CsCl was added to the homogenate and the RNA was pelleted through a pad of CsCl by a high speed centrifugation.

Poly A containing RNA (poly A RNA) was isolated from total RNA by two passages over oligo-dT cellulose, conventionally, and the poly A RNA was size-fractionated by agarose gel electrophoresis, according to standard procedures.

The induced poly A RNA was extracted from the agarose gel essentially as described in Reference 3. Briefly, the gel was melted and then frozen to release the RNA into solution. The solidified agarose was removed by centrifugation. The extracted poly A RNA was extracted with phenol and precipitated with ethanol.

To examine the translation products of the induced poly A RNA in a cell-free protein synthesizing system, antibodies against *A. awamori* glucoamylase were prepared. Glucoamylase-I and II from *A. awamori* were obtained from the filtrate of a culture of *A. awamori* cells grown under glucoamylase induction conditions. The filtrate was fractionated by ion exchange chromatography using a diethylaminoethylcellulose column. Elution with a pH gradient ranging from pH 8.0 to pH 3.0 yielded two protein peaks that showed glucoamylase activity. The enzyme that eluted at the lower pH included the larger glucoamylase-I, and the other peak, glucoamylase-II. Gel electrophoresis indicated that glucoamylase-II was pure, but that glucoamylase-I was not. Glucoamylase-I was purified further by molecular sieve chromatography on a cross-linked dextran, Sepharcryl S-200 column. Two peaks were observed, one of them containing glucoamylase-I, which was shown to be pure. For both enzyme forms, enzyme purity was established by polyacrylamide gel electrophoresis under non-detergent conditions, and by sodium dodecyl sulfate polyacrylamide gel electrophoresis (SDS-PAGE).

The two purified glucoamylase forms were used separately to raise anti-glucoamylase antibodies in rabbits. Each of the two immunoglobulin G(IgG) antibody fractions produced were able to neutralize the glucoamylase activity of both glucoamylase forms. Further, Ouchterlony analysis of the two antibody fractions with the two enzyme forms indicated that each antibody reacts immunospecifically with both enzyme forms.

Poly A RNA from induced and noninduced *A. awamori* was used to direct the synthesis of radioactive-methionine-labeled polypeptides in a rabbit reticulocyte lysate kit obtained from New England Nuclear Co., Boston, Mass., and sold as Reticulocyte Lysate/Methionine L[$^{35}$S]-Translation System. References 4 and 5 describe typical reticulocyte lysate systems. After a defined reaction period, aliquots of the lysate were removed and analyzed, either before or after reaction with anti-glucoamylase antibody or normal rabbit immunoglobulin G (IgG), by SDS-PAGE. The immunoreactive products were precipitated essentially according to the method described in Reference 6.

To determine the molecular basis for the accumulation of glucoamylase protein in starch-grown, but not xylose-grown, cultures of *A. awamori*, glucoamylase mRNA levels were examined. Total cellular mRNA was isolated and used to direct the synthesis of *A. awamori* protein in a rabbit reticulocyte lysate system. The translation products were immunoprecipitated using rabbit anti-glucoamylase antibody (lane 1, xylose-grown cells; lane 3, starch-grown cells) or normal rabbit antibody (lane 2, xylose-grown cells; lane 4, starch-grown cells). The results are shown in FIG. 1 and demonstrate the presence of translatable glucoamylase mRNA in RNA from starch-grown cells. In contrast, no glucoamylase mRNA was detected in xylose-grown cells. This correlates with the 200-fold difference in glucoamylase protein observed in culture supernatants of these cells. Thus, the accumulation of glucoamylase protein in starch-grown cultures appears to result from a comparable increase in translatable glucoamylase mRNA.

Figure 2A:
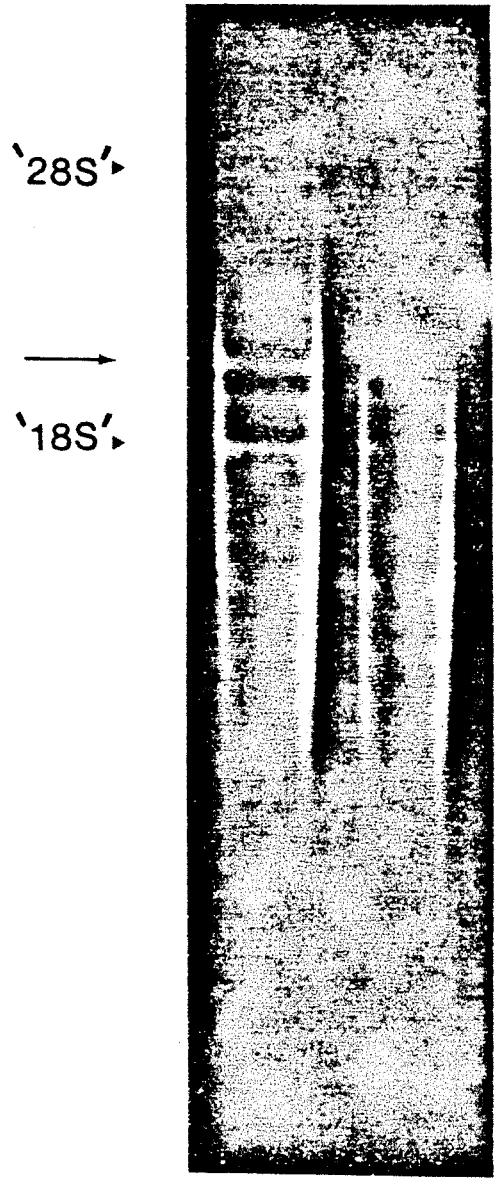
FIGS. 2A and 2B represent gel electrophoretic patterns identifying glucoamylase mRNA.
Figure 2B:
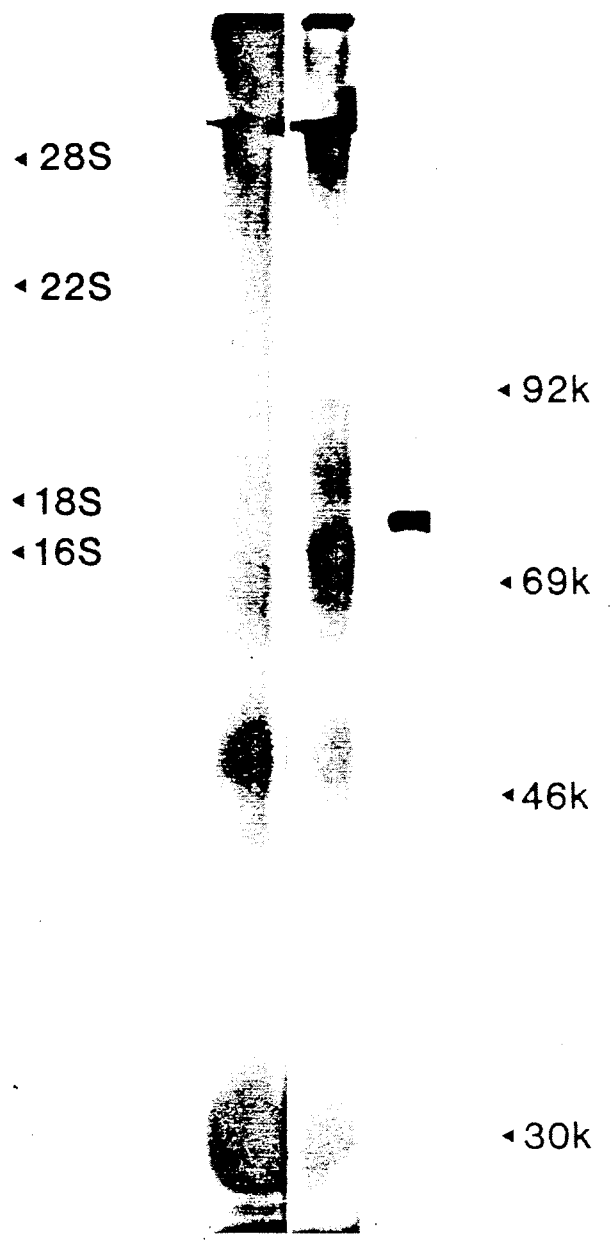

MeHgOH-agarose gel electrophoresis of mRNA from starch-grown cells revealed a major approximately 2.2 kilobase mRNA (indicated by an arrow), which was absent in mRNA from xylose-grown cells (FIG. 2A). It appeared likely that this predominant 'induced' mRNA represented the mRNA of the highly expressed, 'induced' glucoamylase. To identify the 'induced' mRNA, the approximately 2.2-kilobase mRNA band was eluted from a gel and translated in the rabbit reticulocyte lysate system. Immunoprecipitation of the protein product with rabbit anti-glucoamylase antibody demonstrated the presence of mRNA encoding glucoamylase within the approximately 2.2-kilobase 'induced' mRNA band (FIG. 2B).

According to one aspect of the invention, isolated glucoamylase mRNA from the selected fungal species was used to produce a glucoamylase cDNA by reverse transcription of the mRNA. Experimentally, induced poly A RNA from *A. awamori* was pretreated with 10 mM MeHgOH to denature the RNA, and then introduced into a reaction containing oligo-dT as a primer and 2 mM adenosine: $VOSO_4$ as an RNAse inhibitor. The reader is referred to Reference 7 for a discussion of this general technique. Following cDNA synthesis, the poly A RNA was destroyed by treatment with NaOH. The synthesized cDNA was size fractionated by gel electrophoresis to separate the full-length cDNA from incompletely formed fragments. A typical gel electrophoretic pattern of the cDNA fraction showed a single detectable band in the approximately 2.2 kilobase size region.

The induced glucoamylase mRNA and the cDNA produced therefrom were radiolabeled to provide probes for identifying genomic DNA fragments containing all or portions of the homologous glucoamylase gene. The cDNA may be labeled readily by performing its synthesis in the presence of radiolabeled nucleotides.

The basic method used for radiolabeling mRNA is discussed in Reference 8. In one example, induced poly A RNA from *A. awamori* was partially degraded, using sodium hydroxide to generate fragments containing 5'-OH groups. These fragments were subsequently phosphorylated with radioactive-phosphate ($^{32}$P)-ATP using a polynucleotide kinase. The $^{32}$P-labeled RNA fragments span the entire length of the isolated RNA, and are thus advantageous for use as probes for genomic DNA fragments containing end portions of the glucoamylase gene.

Total genomic DNA isolated from *A. awamori* was digested to completion with each of a number of restriction endonucleases. The fragments were size-fractionated by gel electrophoresis and hybridized to one of the above RNA or cDNA probes by the Southern blot method (Reference 9). Details of this method are found generally by Reference 5, at page 387. Briefly, a prehybridization step was performed at 42° C. for 24 hours, using a five-times concentrate of standard salien citrate (0.15M sodium chloride, 0.015M trisodium citrate). This was followed by a hybridization step carried out at 42° C. for 24 hours, using a two-times concentrate of the standard saline citrate. In the studies involving *A. awamori* genomic DNA, several of the endonucleases used--including HindIII, XhoI, BclI, and PvuI--generated only one fragment which hybridized to the above *A. awamori* labeled RNA or cDNA probes. Some of the single gene fragments are in the same size range as the RNA transcript, strongly indicating that *A. awamori* contains only one gene which codes for the glucoamylase polypeptide. EcoRI generated a 3.4 kilobase fragment which hybridized to the labeled cDNA.

The *A. awamori* genomic DNA fragments produced by digestion with EcoRI were spliced, by conventional techniques, into a lambda Charon 4A phage vector. The library of EcoRI fragments were screened for recombinants which hybridized to the *A. awamori* glucoamylase cDNA. Hybridizing plaques were purified, and all contained a common 3.4 kilobase EcoRI fragment which hybridized to the glucoamylase cDNA probe. This 3.4 kilobase EcoRI fragment was then subcloned into the EcoRI site of a pACYC184 plasmid (ATCC Deposit No. 37,033), producing a recombinant plasmid which is designated herein as pGAR1. A sample of *E. coli* K12 strain MM294 transformed with pGAR1 was deposited in the American Type Culture Collection, 12301 Parklawn Drive, Rockville, Md. 20852, USA on Dec. 2, 1983, and has been assigned ATCC Number 39,527. Subsequent libraries were screened using pGAR1 as probe. Approximately 20 kilobases of *A. awamori* genomic DNA surrounding the glucoamylase gene was isolated from EcoRI, HindIII and BglII libraries. A composite restriction map of this 20 kb region is shown in FIG. 3; the EcoRI fragment insert is expanded. The locations of the cleavage sites of the designated restriction endonucleases were determined by digesting the plasmids with selected combinations of the endonucleases, and size-fractionating the fragments obtained, according to known methods. The five solid rectangles represent sequenced protein-encoding regions of the glucoamylase gene. The direction of c transcription of the mRNA is indicated by the 5' to 3' line.

The plasmid pGAR1 was confirmed to contain glucoamyiase gene sequences by virtue of its ability to hybridize to and select *A. awamori* glucoamylase mRNA sequences. pGAR1 DNA was immobilized onto nitrocellulose and hybridized to total *A. awamori* mRNA. The selected mRNA was translated in vitro, and the products were identified by immunoprecipitation with rabbit anti-glucoamylase antibody. The results, shown in FIG. 4, confirm the identification of pGAR1, and thus of the approximately 2.2 kilobase "induced" mRNA, as encoding glucoamylase. In FIG. 4 total *A. awamori* mRNA (lane 1) and mRNA isolated by virtue of hybridization to pGAR1 DNA (lane 2) was translated in vitro and the protein products are displayed. Protein products of lane 2 were immunoprecipitated using rabbit antiglucoamylase antibody (lane 3) or normal rabbit antibody (lane 4).

Figure 6:
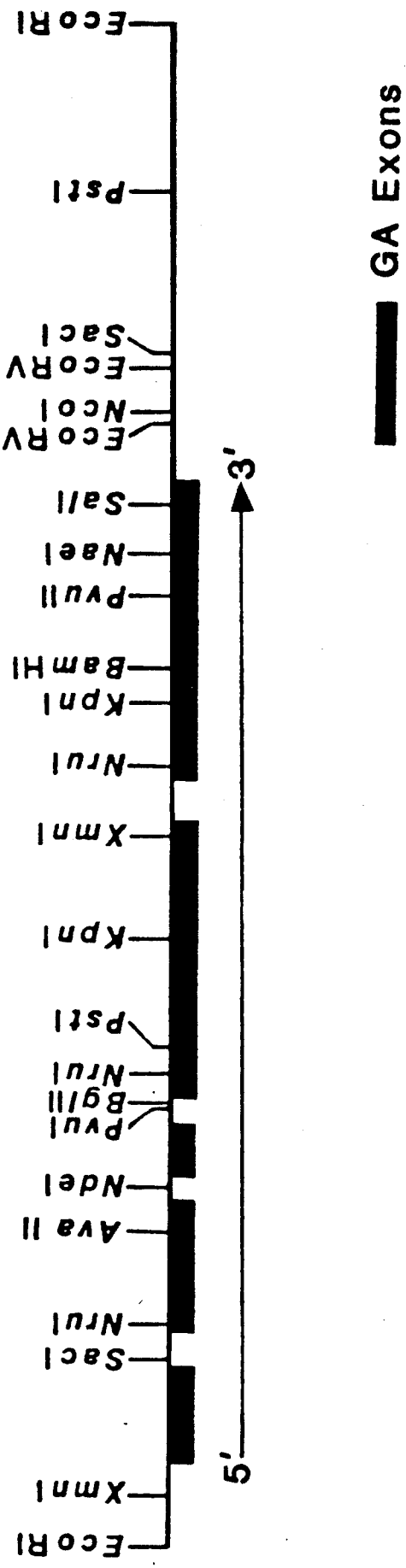
FIG. 6 illustrates a restriction map of the EcoRI fragment containing the genomic glucoamylase gene, where the shaded boxes under the sequence represent the exons or coding regions of the glucoamylase gene and the arrow represents the direction of mRNA transcription.

Subclone pGAR1 containing the *A. awamori* glucoamylase gene was digested substantially to completion with various restriction enzymes whose sequences are included within the EcoRI fragment (i.e., those in FIG. 6), and several of the fragments were subcloned into M13 vectors M13mp8 and M13mp9. These bacteriophage vectors are available from Bethesda Research Laboratories, P.O. Box 6009, Gaithersburg, Md. 20877.

The fragments of the glucoamylase genomic region subcloned into the vectors M13mp8 and M13mp9 were sequenced by the dideoxynucleotide chain termination method described in References 10 and 11. Portions of the sequence were confirmed by the Maxam-Gilbert sequencing technique (Reference 12). The entire sequence of the 3.4 kilobase EcoRI fragment is shown in FIG. 12.

The nucleotide sequence obtained was compared, in a computer-programmed matching operation, with the regions of known amino acid sequence of *A. niger* (References 1a and 1b) and *A. awamori glucoumylase*. The matching operation examined the nucleotide sequence in each of the six possible reading frames for codon correspondence with the given amino acid sequence. The matching operation produced nearly complete correspondence between coding regions of the glucoamylase gene and the regions of known amino acid sequence of glucoamylase from *A. awamori*. The amino acid sequence of one of the internal peptides of *A. niger* (FIG. 7 of Reference 1a) was found not to be contiguously encoded by the nucleic acid sequence (nucleotides 755897 of FIG. 12). An intervening sequence of 55 nucleotides was presumed to interrupt this protein coding region. The introns in the glucoamylase gene are in lower case. The amino acid sequence of the glucoamylase gene is indicated below the appropriate nucleotides and is numbered below the nucleotide sequence numbers at the right. Amino acids −24 to −1 represent the signal sequence of the preglucoamylase protein.

To confirm the identification of this interrupting sequence as the intervening sequence, and to identify other intervening sequences within the glucoamylase gene, the cDNA sequences derived from glucoamylase mRNA were molecularly cloned. Double-stranded cDNA was prepared from mRNA of starch-grown *A. awamori* and a cDNA library was prepared in pBR322, also available from Bethesda Research Laboratories, as described above. Sixteen glucoamylase cDNA-containing plasmids were identified using pGAR1 probe; the largest plasmid, p24A2, which was deposited with the National Regional Research Laboratory in Peoria, Ill., USA on Dec. 7, 1983 and assigned NRRL No. B-14217, contained 1.8 kilobases of sequence derived from the 3' end of the approximately 2.2 kilobase glucoamylase mRNA. The nucleotide sequence of the glucoamylase cDNA in p24A2 was determined and found to span the genomic sequence, shown in FIG. 12, from nucleotide 500 through the polyadenylation site at position 2491-2493. (The precise polyadenylation site cannot be determined unambiguously due to the presence of two A residues at nucleotides 2494-2495.) Comparison of the nucleotide sequence of the molecularly cloned glucoamylase gene with that of the glucoamylase mRNA, as determined from molecularly cloned glucoamylase cDNA, and with glucoamylase amino acid sequence, has revealed the presence of four intervening sequences (introns) within the *A. awamori* glucoamylase gene. (The junctions of the first intervening sequence were deduced from incomplete amino acid sequence data at residues 43–49 of *A. awamori* glucoamylase-I.) The intervening sequences were short (ranging from 55 to 75 base pairs) and were all located within protein-encoding sequences. These sequences adjoining the intervening sequence junctions of the glucoamylase gene were compared to consensus splice junction sequences from eucaryotes in general (Reference 13) and from *S. cerevisiae* in particular (Reference 14). Splice junctions within the glucoamylase gene conform closely to the consensus sequences at the 5' and 3' intervening sequence termini. Sequences related to the consensus sequence TACTAACA postulated by Langford, et al. in Reference 15 to be required for splicing in *S. cerevisiae* are found near the 3' terminus of all glucoamylase intervening sequences.

Figure 5:
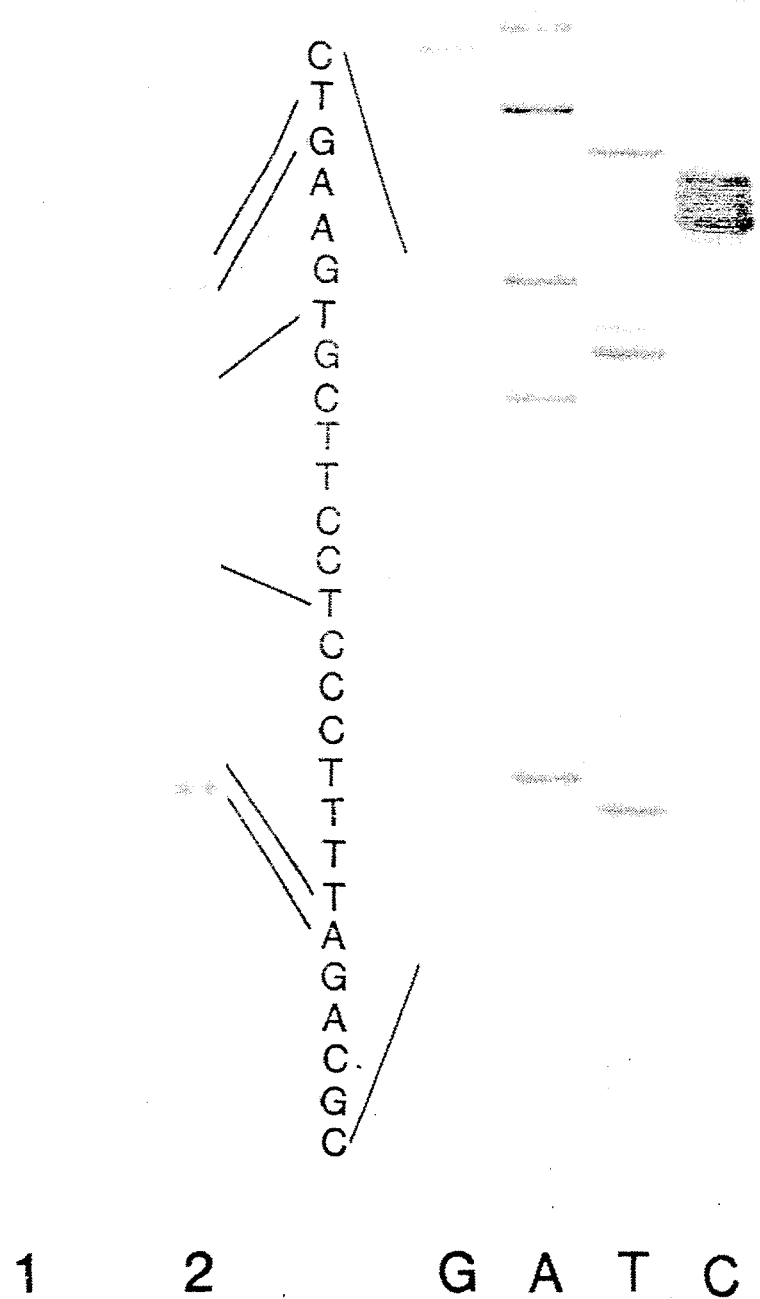
FIG. 5 illustrates primer extension to determine 5' termini of glucoamylase mRNA and the sequence which was determined. The products of primer extension at 42° C. (lane 1) and 50° C. (lane 2) are displayed on a sequencing gel in parallel with m13/dideoxynucleotide sequencing reactions of this region, utilizing the identical 15-mer primer. The sequence presented represents the glucoamylase mRNA sequence and is complementary to that read from the sequencing reactions shown.

The 5' end of the glucoamylase mRNA was determined using a synthetic oligonucleotide to prime reverse transcriptase synthesis from the mRNA template. Four major primer extension products were synthesized using the pentadecamer 5'GCGAGTAGAGATCGG3' which is complementary to sequences within the signal peptide-encoding region near the 5' end of the glucoamylase mRNA, as indicated in FIG. 5.

The shorter band of the doublets is interpreted to represent the incompletely extended form of the longer band. To examine possible effects of RNA secondary structures on this pattern, primer extension was preferred at 42° and 50° C. The products of primer extension at 42° C. (lane 1) and 50° C. (lane 2) are displayed on a sequencing gel described in Reference 16 in parallel with m13/dideoxynucleotide sequencing reactions of this region, using the identical pentadecamer primer. The sequence presented in FIG. 5 represents the glucoamylase mRNA sequence and is complementary to that read from the sequencing reactions shown. The pattern of primer extension was unchanged, supporting the conclusion that four distinct 5' termini exist within the population of glucoamylase mRNA. Primer extension reactions performed in the presence of dideoxynucleotides confirmed the colinearity of genomic and mRNA sequences in this region. The primer extension products map to T residues, at positions −71, −66, −59, and −52 from the site of translation initiation, as indicated in FIG. 12. To the extent that reverse transcriptase is able to copy the extreme terminal nucleotide(s) of the mRNA, the 5' termini of the glucoamylase mRNAs are localized to these four regions. DNA sequences 5' of the region of transcription initiation were found to contain sequences homologous to consensus sequences previously shown to be involved in transcription initiation by RNA polymerase II.

FIG. 13 illustrates the nucleotide sequence encoding the mature glucoamylase polypeptide.

Nucleotides 206 to 277 encode the signal sequence for the *A. awamori* glucoamyulase. As used in the specification and claims, the term "signal sequence" refers generally to a sequence of amino acids which are responsible for initiating export of a protein chain. A signal sequence, once having initiated export of a growing protein chain, is cleaved from the mature protein at a specific site. The term also includes leader sequences or leader peptides. The preferred signal sequence herein is the deduced signal sequence from the *A. awamori* glucoamylase gene given in Table.

TABLE I

| MET SER PHE ARG SER LEU LEU ALA LEU SER GLY LEU VAL CYS THR |
| GLY LEU ALA ASN VAL ILE SER LYS ARG |

EXAMPLE 2

Expression of Glucoamylase Gene in Yeast

A. Construction of HindIII Cassette of Genomic Glucoamylase Gene

A method for expressing genes at high levels in yeast involves constructing vectors which contain the yeast enolase I promoter and terminator regions (Reference 16). The enolase segments were previously engineered so that the promoter and terminator were separated by a unique HindIII site.

Plasmid pAC1 (10.67 kb) is an E. coli/yeast shuttle vector, capable of autonomous replication in both *E. coli* and yeast strains. The plasmid confers resistance in *E. coli* and related species to the β-lactam antibiotic ampicillin and related compounds as a result of synthesis of the TEM type I β-lactamase. Further, the plasmid carries the yeast LEU2 gene which is expressed in both *E. coli* and *S. cerevisiae* strains. Thus, the presence of the plasmid in either *E. coli* or *S. cerevisiae* strains reverses a leucine growth requirement resulting from loss of β-isopropylmalate dehydrogenase activity.

Plasmid pAC1 is comprised of the following DNA segments. Numbering starts at the EcoRI site of the enolase I promoter fragment and proceeds in a clockwise direction. Coordinates 0 to 725 comprise a 725 base pair EcoRI to HindIII DNA fragment derived from a similar fragment in the plasmid p eno 46 (Reference 16), containing DNA from the 5' untranslated region of the *S. cerevisiae* EnoI gene. This fragment has been modified in the region just prior to the initiation codon (ATG) of the enolase gene in order to create a HindIII site. Specifically, the sequence was changed from CACTAAATCAAAATG to CACGGTCGAGCAAGCTT(ATG). Coordinates 726 to 2281 comprise the 1.55 kb HindIII to BglII DNA fragment from the 3' untranslated region of the *S. cerevisiae* EnoI gene and was originally obtained from the plasmid peno 46 (Reference 16). Coordinates 2282 to 2557 comprise a 275 bp DNA fragment from the plasmid pBR322 (Reference 16a) between the BamHI and SalI recognition sites (pBR322 coordinates 375 to 650). Coordinates 2558 to 4773 comprise the 2.22 kb XhoI to SalI DNA fragment from *S. cerevisiae* that encodes the LEU2 gene product, β-isopropylmalate dehydrogenase. The plasmid YEp13 (Reference 16b) provided a convenient source for the desired 2215 bp DNA fragment. Coordinates 4474 to 8528 comprise a 3.75 kb DNA fragment which permits autonomous replication of the plasmid ACI in yeast strains. This region encodes a portion of the yeast 2μ plasmid and was derived from the plasmid pDB248 (Reference 16c). Digestion of plasmid pDB248 with the enzymes EcoRI and SalI liberated the desired 3.75 kb DNA fragment incorporated in plasmid ACI. Coordinates 8529 to 10672 comprise DNA sequences which permit autonomous replication in *E. coli* host strains and confer ampicillin resistance. The desired 2143 bp DNA fragment was obtained from *E. coli* plasmid pBR322 as a Tth111I to EcoRI DNA fragment (pBR322 coordinates 2218 and 4360, respectively). A sample of *E. coli* K12 strain MM294 transformed with pACI was deposited in the American Type Culture Collection on Dec. 2, 1983 and has been assigned ATCC No. 39,532.

The glucoamylase gene, while not having a convenient restriction site closely preceding its initiation codon (ATG) useful for cloning into vectors, can have a single base pair change 32 base pairs upstream from the ATG so as to create a unique HindIII site, allowing use of the enolase promoter for initiation of transcription. Site-specific mutagenesis was used to obtain the desired mutation. A hexadecamer oligonucleotide which is complementary to the region surrounding the desired HindIII site and which contains the appropriate mismatch was used to prime DNA synthesis on a single-stranded M13 template of the glucoamylase gene. The sequence of the primer employed was : GAGC-CGAAGCTTCATC, with the mismatches underlined. A second mismatch was incorporated into the primer to aid in the screening for correct clones by hybridizing candidate plaques with the same oligonucleotide used for the primer extension, after the latter had been radioactively labeled.

One picomole of a single stranded DNA phage, M13mp9 containing a 2.3 kb glucoamylase gene fragment (from EcoRI to SalI), was annealed to 10 picomoles of the primer in a 15 µl reaction mix which also contained 20 mM Tris pH 7.9, 20 mM MgCl$_2$, 100 nM NaCl, and 20 mM β-mercaptoethanol. The mixture was heated to 67° C., incubated at 37° C. for 30 minutes, then placed on ice.

To the above annealing mixture 1 µl of each deoxynucleotide triphosphate at 10 mM was added, to a final concentration of 500 µM. Five units of *E. coli* Klenow fragment of DNA polymerase I (0.5 µl) was then added and the extension reaction was left on ice for 30 minutes. Starting on ice minimizes 3'-5' exonuclease digestion of the primer and subsequent mismatch correction. After 30 minutes on ice, the reaction was continued at 37° C. for 2 hours, then inactivated by heating at 67° C. for 10 minutes.

Note that the primer was not kinased and no ligase was used in contrast to other published methods. JM103 competent cells were transformed with 1 µl of the reaction and either 5 µl or 50 µl were plated.

The hexadecamer used for priming was kinased with labeled $^{32}$P-ATP to a specific activity of $3 \times 10^7$ cpm/µg. Nitrocellulose filters were used to bind phage DNA from the plaques by direct lifting, and these filters were denatured, neutralized and washed in the usual way. After baking for 2 hours at 80° C., the filters were prehybridized for 3 hours at 45° C. in 25 ml of 6×SSC, 0.1% SDS, 5×Denhardt's, 50 µg/ml yeast RNA. After prehybridization, $1.5 \times 10^5$ cpm/ml of kinased primer was added, and hybridization continued overnight at 45° C. The next day, filters were washed 2 times, 5 minutes each in 6×SSC at roughly 5° C. (to remove non-specifically bound counts), then once at 45° C. for 5 minutes (to remove probe hybridized to non-mutant phage DNA). Filters were air dried, put on XAR film with an intensifying screen and exposed overnight at −70° C.

One mutant clone among several thousand plaques was discovered in the first round of screening. Subsequent restriction enzyme digests of this clone confirmed the introduction of the HindIII site in front of the glucoamylase gene.

Figure 7:
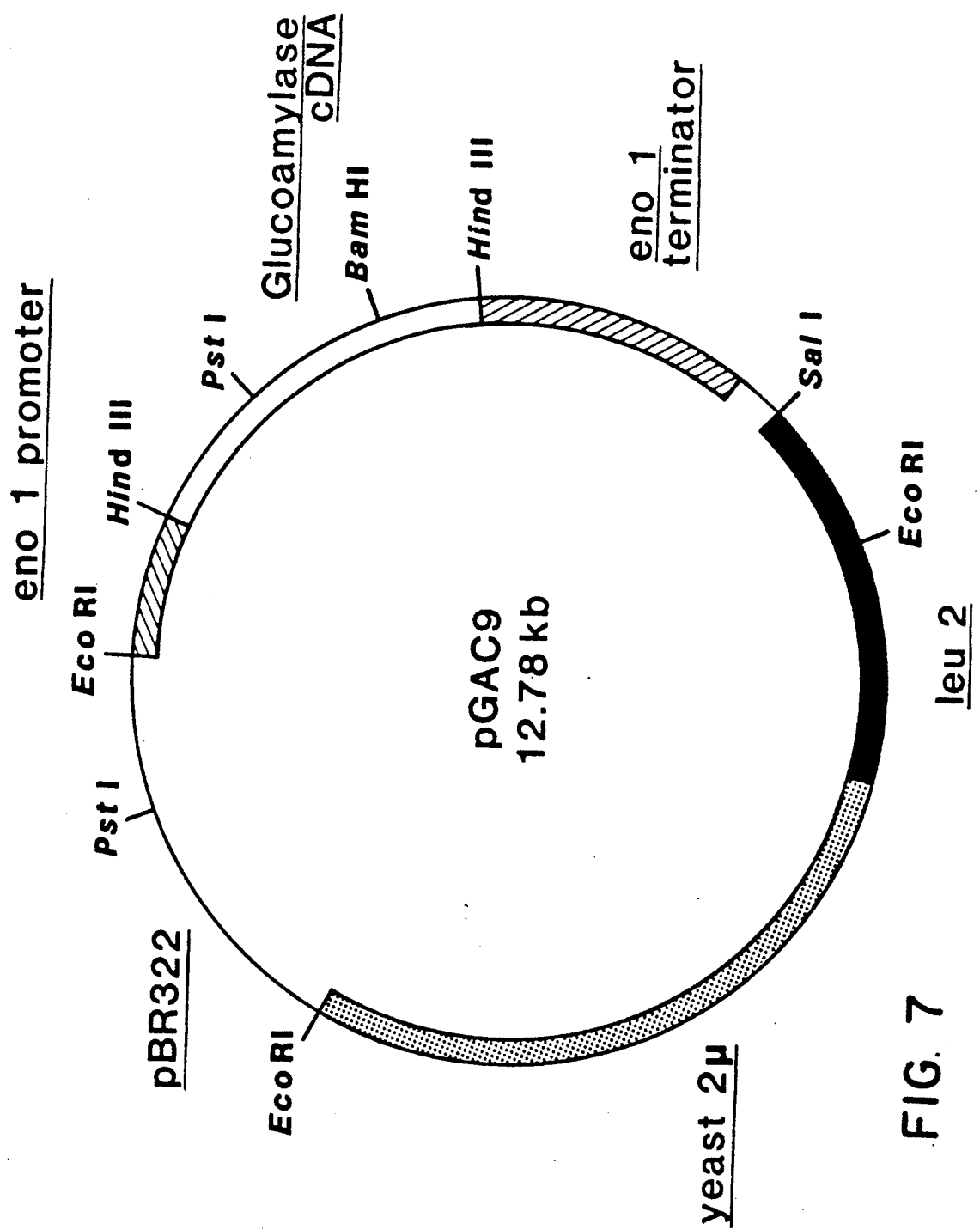
FIG. 7 illustrates a plasmid map for pGAE9.

In the next step a HindIII site was created at the 3' end of the glucoamylase gene. A clone with the engineered HindIII site near the 5' end of the gene was cut with NcoI, its sticky ends were converted to blunt ends by enzymatic repair using Klenow fragment of *E. coli* DNA polymerase-I, and it was cut with EcoRI. FIG. 7 illustrates a restriction map of this region. This method produced a fragment containing the glucoamylase gene and having an EcoRI sticky end before the 5' end of the gene and a blunt end after the 3' end of the gene. This fragment was cloned into a polylinker region of plasmid pUCB, available from Bethesda Research Laboratories, to place a HindIII site within 20 nucleotides of the 3' end of the fragment so as to produce a HindIII cassette.

B. Construction of Full-Length cDNA Clone of Glucoamylase Gene Lacking Introns The longest cDNA clone produced and isolated which had regions homologous to the genomic clone of the glucoamylase gene, p24A2, corresponds in sequence to the genomic clone from nucleotides 501 to 2490, minus the nucleotides corresponding to introns indicated in lower case in FIG. 12. This clone is still several hundred nucleotides shorter than necessary for a full-length cDNA clone. The construction of a full-length cDNA copy of the gene was accomplished in several steps. The genomic clone with the HindIII site near the 5' end of the gene was cut with EcoRI and AvaII and this fragment was purified. The longest cDNA clone described above was digested with AvaII and PstI, and the small AvaII to PstI fragment was purified. The phage vector M13mp11, available from P-L Biochemicals, 1037 W. cKinley Ave., Milwaukee, Wi. 53205, was digested with EcoRI and PstI, and the large vector fragment was purified from the small polylinker fragment. These three fragments were ligated together to generate a M13mp11 vector containing the EcoRI and PstI region of the genomic clone, but now missing the second intron.

The longest cDNA clone was then cut with PstI using conditions supplied by the manufacturer of the restriction enzyme and the large PstI fragment was isolated. The M13mp11 vector described above was cut with PstI, and the large PstI fragment from the cDNA clone was ligated into this site. The clones generated from this ligation were screened to identify the clone with the PstI fragment inserted in the correct orientation. The clone isolated from this step had the genomic sequence from EcoRI to AvaII (containing the first intron and the new 5' HindIII site) and the cDNA sequence from AvaII to the PstI site beyond the poly-A tail region. The remaining intron at the 5' end of the gene was removed by site-directed mutagenesis using a nonacosamer oligonucleotide to span the intron region. The nonacosamer, which had homology to 15 base pairs on the 5' side of the intron and 14 bas pairs on the 3' side, had the sequence:

5'*CGGATAACCCGGACTACTTCTACACCTGG* 3'

In the procedure for conducting site-directed mutagenesis, one picomole of a single-stranded DNA phage derivative designated as M13mp9 (which is commercially available), containing a 2.3 kb glucoamylase gene fragment (from EcoRI to SalI), was annealed to 10 picomoles of primer in 15 µl containing 6 mm of tris(hydroxy methyl)aminomethane (hereinafter Tris) at pH 7.9, 6 mm MgCl₂ and 100 mM NaCl. The mixture was heated to 67° C., incubated at 37° C. for 30 minutes, and then placed on ice. At this temperature, either half of the nonacosomer can anneal to its complement on the template without the other, allowing the proper loop to be formed.

To the above annealing mixture 1 μl of each deoxynucleotide triphosphate at 10 mM was added, to a final concentration of 500 μM. Five units of *E. coli* Klenow fragment of DNA polymerase I (0.5 μl) was then added and the extension reaction was left on ice for 30 minutes to minimize 3'-5' exonuclease digestion of the primer. After 30 minutes on ice, the reaction was continued at 37° C. for 2 hours, and then inactivated by heating at 67° C. for 10 minutes.

In the procedure employed herein the primer was not kinased and no ligase was employed in contrast to other published methods. JM 103 competent cells were transformed with 1 μl of the reaction and either 5 μl or 50 μl were plated. (JM103 is an *E. coli* strain distributed by Bethesda Research Laboratories, Inc., Gaithersburg, Md. 20877.)

The nonacosamer used for priming was kinased with labeled $^{32}$P-ATP to a specific activity of $3 \times 10^7$ cpm/μg. Nitrocellulose filters were employed to bind phage DNA from the plaques by direct lifting, and these filters were denatured, neutralized and washed. After baking for 2 hours at 80° C., the filters were prehybridized for 3 hours at 55° C. in 25 ml of a solution of 9 M NaCl and 0.9 M sodium citrate, 0.1% sodium dodecyl sulfate, 50 ml of a solution containing 0.5 g bovine serum albumin, 0.5 g Ficoll 400 (which is a carbohydrate polymer obtainable from Pharmacia Fine Chemicals) and 0.5 g polyvinylpyrrolidone, and finally 50 μg/ml yeast RNA. After prehybridization, $1.5 \times 10^5$ cpm/ml of kinased primer was added, and hybridization was continued overnight at 55° C.

The next day, the filters were washed two times for five minutes each in a solution of 9 M NaCl and 0.9 M sodium citrate at roughly 5° C. (to remove non-specifically bound counts), and then once at 55° C. for five minutes (to remove probe hybridized to non-mutant phage DNA). Filters were air-dried and placed on Kodak XAR (high speed) film with an intensifying screen and exposed overnight at −70° C.

The frequency of positives recovered was about 4%. Positive candidate plaques were further examined by preparing mini-preps and digesting them to see if a size reduction occurred due to removal of the 75 base pair intron. Sequencing of one of the positives revealed that the intron had been precisely removed.

In the final step this plasmid vector was digested with EcoRI and BamHI, and the fragment was purified and used to replace the EcoRI to BamHI fragment in the genomic HindIII cassette vector described under section A above. The result is a cDNA HindIII cassette which will have the normal polyadenylation signal at the 3' end of the clone but lacks all four introns.

C. Yeast Strains Transformed with Yeast Expression Vector

Figure 8:
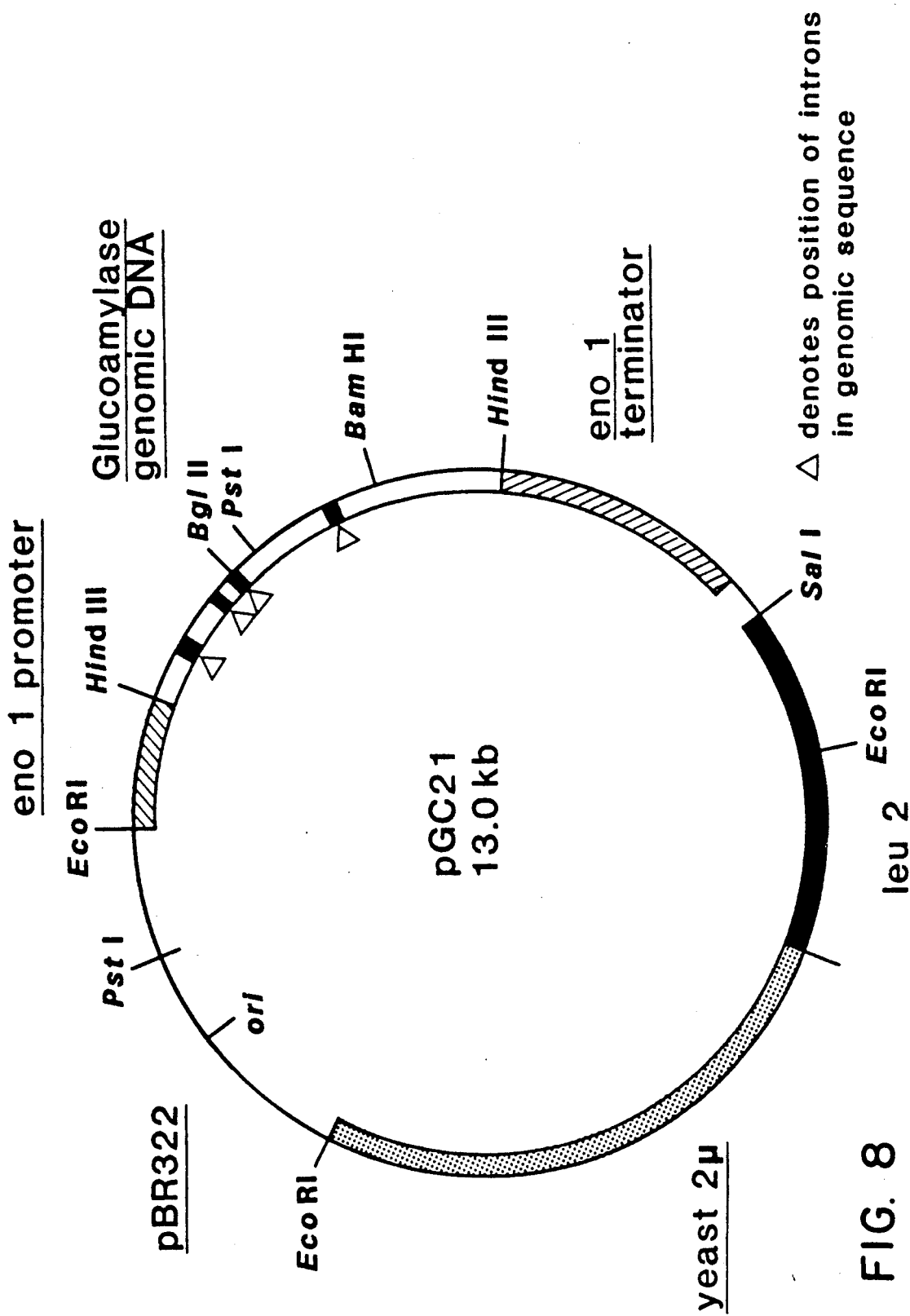
FIG. 8 illustrates a plasmid map for pGC21.

The intron-containing HindIII cassette of the genomic glucoamylase gene as described in section A above was excised and inserted into a yeast expression vector plasmid pACI to produce a plasmid designated as PGC21, the map of which is presented in FIG. 8. A sample of *E. coli* K12 strain MM294 transformed with pGC21 was deposited in the NRRL on Dec. 7, 1983 and has been assigned NRRL No. B-14215. A sample of *E. coli* K12 strain MM294 transformed with pAC1 was deposited in the American Type Culture Collection on Dec. 2, 1983 and has been assigned ATCC No. 39,532. The cassette of full-length cDNA clone lacking introns as described in section B above was similarly excised and inserted into the vector pACI to produce a plasmid designated as pGAC9, the map of which is presented in FIG. 7.

Plasmid DNAs pGAC9 and pGAC9 were amplified in *E. coli*, purified on a cesium chloride gradient and used to transform two strains of yeast: yeast strain C468, which is a haploid *Saccharomyces cerevisiae* with auxotrophic markers for leucine and histidine, and yeast strain H18, which is a haploid *S. cerevisiae* with auxotrophic markers for leucine and histidine, which lacks the repressor for the glucoamylase gene of *Saccharomyces diastaticus*. Leu⁺ transformants were screened for expression of the *Aspergillus awamori* glucoamylase gene. H18 was deposited in the National Regional Research Laboratory in Peoria, Ill., USA on Dec. 7, 1983 and has been assigned NRRL Number Y-12842.

Yeast strains which were transformed with the yeast expression vectors pGC21 and pGAC9 were compared with the same strains transformed with the parent plasmid pAC1 as a control for growth on various starches in liquid and on solid media. Three types of starch were used: "washed" starch (a soluble starch washed three times with 70% ethanol to remove sugars and short chain carbohydrates), cassava starch, and soluble potato (Baker's) starch. Yeasts transformed with any of the three plasmids grew on the three starches; however, the cDNA clones (pGAC9) always showed better growth than the other clones, both in liquid and on solid media. When Baker's starch, which is the most highly polymerized of the three starches, was used in solid media at a concentration of 2% (w/v), the plates were turbid. These plates were spread with yeast from both strains carrying the parent plasmid, the genomic clone or the cDNA clone, and with yeast strain *Saccharomyces diastaticus*, having NRRL Deposit No. Y-2044, which expresses a yeast glucoamylase. The plates are shown in FIG. 9. The strains carrying the cDNA clone (pGAC9) were able to clear the starch around the growth zone, indicating that they could degrade the starch completely. In contrast, the *S. diastaticus* strain and the yeast strains transformed with either the parent plasmid pACI or the genomic clone pGC21 were unable to clear the starch from around the growth area. The clearing of the highly polymerized starch exhibited by pGAC9-containing strains indicates the functional expression of the *A. awamori* glucoamylase gene that has both alpha 1-4 and alpha 1-6 amylase activity.

In another test for glucoamylase expression, yeast cells carrying the control plasmid, pACI, or the cDNA clone, pGAC9, were grown in a washed starch liquid medium. The cells were harvested and lysed by ten cycles of freeze, thaw, and vortexing with glass beads. Each cell lysate, containing intracellular proteins, was electrophoresed on a 7% acrylamide gel containing 0.1% sodium dodecyl sulfate (SDS) and 7.6 M urea and transferred to cellulose paper activated with cyanogen bromide. After the proteins were transferred, the paper was first probed with antiserum from a rabbit immunized against *A. awamori* glucoamylase and then with radioactively labeled Staph A protein that binds to antibody molecules. After unbound radioactivity was washed off, the paper was dried and exposed to X-ray film. This technique, which is called a "Western" and is described in Reference 17, can be performed with antiserum or purified antibody. Protein that reacts with glucoamylase antisera was detected in the lysates from the pGAC9 cDNA clones but not in the pACI controls.

The expression of the *A. awamori* glucoamylase gene was also tested directly by the ability of a yeast containing such a gene to grow on an otherwise non-utilizable carbon source. For yeast strains C468 and H18, this growth test was accomplished using maltose as the carbon source, because both of these strains carry a mutation (mal) blocking the utilization of maltose as a carbon source. The ability of strains C468 and H18 containing the control plasmid pAC1 or the cDNA plasmid pGAC9 to grow on maltose and glucose as a carbon source is indicated in Table II. The glucose plates contained histidine while the maltose plates contained both histidine and leucine supplementation. From this table it can be seen that the presence of the glucoamylase gene on the plasmid allows C468 to grow slowly on maltose and H18 to grow slightly better than the control.

These tests indicate that the presence of the glucoamylase gene complements the mal mutation in C468 and facilitates direct selection experiments where the growth of the yeast is solely dependent on proper and adequate functioning of the *A. awamori* glucoamylase gene.

All of these experiments demonstrate that yeast strain C468 containing the plasmid pGAC9 is most superior in expressing the glucoamylase gene. A sample of yeast strain C468 transformed with pGAC9 was deposited with the American Type Culture Collection on Nov. 17, 1983 and has been assigned the ATCC Deposit No. 20,690.

D. 1. Characterization of Glucoamylase Activity in Yeast Cultures

Standing cultures of yeast strain C468 containing pACI or containing pGAC9 prepared as described above were grown in minimal media with glucose or washed Difco soluble starch as the carbon sources. The cultures were harvested, after 5 days for the glucose cultures and after 7 days for the starch cultures, and cell-free supernatants were prepared by centrifugation. These supernatants were concentrated 10–20 fold using an Amicon concentrator with a PM10 membrane. Glucoamylase assays were negative for the supernatants from the glucose- and starch-grown cultures of yeast strain C468 containing pACI plasmid. In contrast, cells containing the control plasmid pGAC9 secreted approximately six units of glucoamylase activity per liter. (For a definition of a unit of glucoamylase activity, see the legend to Table III).

Glucoamylase production in aerobic shake-flask cultures of yeast strain C468 containing pGAC9 plasmid was then assayed. After two days of incubation at 30° C. and agitation at 250 rpm, the culture of C468 yeast strain containing pGAC9 had consumed all of the glucose and was in stationary phase. The culture had achieved a cell density of approximately 2 g/liter dry weight. A glucoamylase assay on the unconcentrated supernatant indicated that approximately 47 units of activity per liter of supernatant was produced.

2. Location of Glucoamylase Activity in Cultures of Transformed Yeast Cells

The experiment given below was used to resolve whether the majority of the glucoamylase activity is found in the culture medium or inside the cell.

Strains C468-pGAC9 and C468-pACI were grown in 500 ml of medium containing 1.45 g of Difco Yeast nitrogen base (Difco Laboratories, Detroit, Mich. 48232), 5.2 g of ammonium sulfate and 2% glucose per liter to a cell density of $2-3 \times 10^7$ cells per ml. The cultures were centrifuged at 4° C. and the supernatants and cell pellets were processed separately. The supernatant samples were filtered through a 0.45 $\mu$ filter and then concentrated 15 to 20× using an Amicon stirred cell with a PM-10 membrane. The cell pellet was washed once in 1 M Sorbitol 0.1 M phosphate buffer pH 7.5 and then the packed cell volume was determined by centrifuging at approximately 1000×g for 5 minutes in a conical graduated centrifuge tube. Each ml of packed cells was resuspended to 1.5 ml in 1.0 M Sorbitol-0.1 M phosphate buffer at pH 7.5 and and equal volume of Zymolyase 5000 (Miles Laboratory, Elkhart Ind. 46515) was added. The cells were gently mixed at room temperature for 1 hr and then centrifuged at 500×g to recover the protoplasts. The supernatant, representing the protein that was present between the cell wall and the inner membrane, was put on ice for later processing. The space between the cell membrane and wall in yeast is referred to as the interstitial space and this protoplast supernatant sample will be referred to as the interstitial sample in the following text. The protoplasts were resuspended in 1 M Sorbitol-0.1 M KPO$_4$ buffer-10 mM NaN$_3$ and washed 1×by centrifuging at 500×g. The pellet was resuspended in 5 ml 1 M Sorbitol-0.1 M KPO$_4$ at pH 7.5–10 mM NaN$_3$ and 1 ml was used to assay the glucoamylase activity present in the intact, azide-treated protoplasts. To the remaining 4 ml of protoplast 4 ml of 50 mM Tris at pH 7.4–10 mM EDTA was added along with 6 g of sterile glass beads (0.45–0.5 mm B. Braun) and the mixture was vortexed vigorously for 20 seconds, cooled on ice and this procedure was

TABLE II

| | | Growth Response of Strain** | | | | | | | |
|---|---|---|---|---|---|---|---|---|---|
| | | Carbon Source | | | | | | | |
| Yeast | | Glucose | | | Maltose | | | | |
| Strain | Plasmid | day 2 | day 4 | day 6 | day 2 | day 4 | day 6 | day 10 | day 13 |
| C468 | pAC1* | ± | + | + | 0 | 0 | 0 | 0 | 0 |
| C468 | pGAC9 | ± | + | + | 0 | 0 | m | ± | + |
| H18 | pAC1* | ± | + | + | 0 | 0 | 0 | 0 | 0 |
| H18 | pGAC9 | ± | + | + | 0 | 0 | 0 | 0 | m |

*Control
**0 = no visible colonies
m = minute colonies < 0.3 mm
± = small colonies < 1 mm
+ = normal colonies 2–3 mm repeated until microscopic observation revealed membrane ghosts or particles but few or no intact protoplasts. Sterile 2 M sucrose was added slowly with a pasteur pipette inserted to the bottom of the tube and the lysate was floated out of the glass beads. The lysate was removed to a new tube and centrifuged along with the interstitial sample at approximately 20,000×g for 30 min at 4° C. The supernatant from the broken protoplasts was designated the intracellular sample and the pellets from the interstitial sample and the broken protoplast sample were combined to make the membrane sample. Thus the yeast culture has been fractionated into five samples: the extracellular or supernatant sample, the interstitial, membrane associated and intracellular samples, as well as a sample containing intact azide-treated protoplasts.

The culture samples were analyzed for glucoamylase activity utilizing the peroxidase-glucose oxidase (PGO)-/o-dianisidine (ODAD) assay (Sigma Kit #510) which detects glucose released from soluble starch by the glucoamylase. The assay can be affected by other enzymes present which utilize glucose or by glucose present in the samples. Each PGO-ODAD Assay mix was tested with known quantities of glucose (generally a dilution series from 0 to 550 nanomoles) and a standard curve was constructed. One glucoamylase unit is defined as the amount of glucoamylase which releases one μmole of glucose per minute from washed soluble starch at 37° C.

Samples were reacted with washed soluble starch on the day they were prepared, then boiled and frozen at −20° C. for later glucose assay. A portion of each fresh sample was precipitated by addition of 3 volumes of cold 95% ethanol, then allowed to stand overnight and the precipitate was collected by centrifugation at 2000×g for 5 min at 4° C. The supernatant sample required a second centrifugation to recover small flocs which remained suspended in the ethanol supernatant. The pellets were dried and then resuspended in 50 mM Tris at pH 7.4–10 mM EDTA to one half their original volume, except the supernatant sample which was resuspended to one twentieth its original volume. These ethanol-precipitated samples were reacted with washed soluble starch and then boiled and frozen −20° C. for assay with the fresh samples.

Intact azide-treated protoplasts were assayed in a reaction mix containing 1 M Sorbitol-0.5% washed starch and 200 μl of protoplasts. These mixes were incubated at 37° C. for 30 min, then centrifuged at 500×g and the supernatant was filtered, then boiled and assayed or stored at −20° C. These assays revealed that the reaction mix contained some residual glucose and that the protoplasts reduced the amount of glucose in the mix during incubation. When lysed protoplasts were incubated in the same mix, more glucose was utilized than when the protoplasts were intact. Values for the glucoamylase plasmid carrying strain were similar to those for the strain carrying the same plasmid without the glucoamylase DNA insert, implying that little, if any, glucoamylase activity is associated with the membrane.

The fresh fractionated samples were assayed and the intracellular samples were found to have residual glucose levels that were too high for the assay. Membrane-associated and interstitial samples from pGAC9- and pAC1-transformed cells both failed to produce detectable levels of glucose from soluble starch. The supernatant sample from pGAC9-transformed yeast demonstrated glucoamylase activity of about 22 units/liter, while the sample from pACI-transformed yeast showed no glucoamylase activity. Ethanol-precipitated samples from the pACI-transformed yeast showed negligible (less than or equal to 0.08 units/liter) or no glucoamylase activity. Ethanol-precipitated samples from yeast transformed with pGAC9 all demonstrated glucoamylase activity of 0.15 units per liter or higher. The supernatant sample contained over 90% of the total glucoamylase activity and the intracellular, membrane associated and interstitial samples contained from 1 to 4% of the total activity depending on the sample. Therefore, most of the glucoamylase enzyme is secreted into the extracellular medium.

E. Production of Recombinant Glucoamylase from Yeast in a 10 Liter Fermentor To produce sufficient glucoamylase for characterization, a 10-liter fermentation of C468 yeast strain containing pGAC9 in minimal media with glucose as the sole carbon source was set up. A 100-ml seed culture was grown in minimal media to an optical density at 680 nm ($OD_{680}$) of 6 and added to the fermentor. The fermentor was run as an aerobic batch fermentation until it reached an $OD_{680}$ of 10, and then a glucose feed was begun. The glucose feed was continued to an $OD_{680}$ of approximately 30 and then stopped, allowing the residual glucose to be consumed. Total fermentation time was approximately 32 hours. The final cell density was approximately 10 g/liter dry weight. Diluted samples of the unconcentrated fermentor supernatant were assayed for glucoamylase activity, with the assay data given in Table IV. The supernatant was concentrated 15-fold using an Amicon Hollow Fiber Concentration unit with a 10,000 molecular weight size exclusion.

The concentrated fermentor supernatant was adjusted to 50 mM phosphate, pH 7.5, by adding concentrated buffer thereto and was

TABLE III

| | Recombinant Glucoamylase Purification | | | | |
|---|---|---|---|---|---|
| Sample | Glucoamylase Activity (units)* | Volume (ml) | Protein (mg)** | Percent Recovery | Specific Activity (units/mg) |
| Fermentor Supernatant | 3146 | 10,000 | — | 100 | — |
| Concentrated Supernatant | 1605 | 660 | 219 | 51 | 7.3 |
| DEAE-Sepharose Column | 2300 | 160 | 173 | 73 | 13.3 |

*One unit of glucoamylase activity is the release of 1 μmole glucose/minute from washed Difco soluble starch in 0.1 M citrate buffer, pH 5.0, at 37° C.
**The protein concentration of the concentrated supernatant was determined using a BioRad protein assay kit. The protein concentration from the DEAE-Sepharose column was estimated by integration of area under the $OD_{280}$ peak (1 $OD_{280}$ units = 1 mg/ml protein).

loaded on a DEAF Sepharose (CL-6B) column. The column was eluted with a pH gradient (starting pH 75, final pH 3.0). The elution profile is shown in FIG. 10. Various samples from the column were analyzed by SDS-urea polyacrylamide gel electrophoresis. A photograph of the gel stained with BioRad silver stain showed that the concentrated fermentor supernatant contained only a few proteins, demonstrating that the glucoamylase was secreted into the media and not released by cell lysis. A comparison of a sample from this concentrated fermentor supernatant with an equal volume of the peak fraction of glucoamylase activity indicated a considerable increase in the purity of the proteins. Estimates indicated that 20-30% of the supernatant protein was glucoamylase and the peak fraction was approximately 80% glucoamylase. The recombinant glucoamylase migrated with a mobility slightly slower than the *A. awamori* glucoamylase, indicating that the glucoamylase produced in the transformed yeast was also glycosylated.

An assay on the peak column fraction of glucoamylase activity indicated that the recombinant glucoamylase has a specific activity comparable to native *A. awamori* glucoamylase, namely 25-50 units/mg.

Experiments prove that the recombinant glucoamylase produced by yeast C468/pGAC9 is glycosylated. Duplicate samples of *A. awamori* glucoamylase-I and glucoamylase-II and the recombinant glucoamylase were electrophoresed in a 10% polyacrylamide-SDS gel using standard procedures. After electrophoresis, the gel was split and lanes 1-4 were stained for protein with a Coomassie Blue stain and lanes 5-7 were stained for carbohydrate with Periodic Acid Schiff's stain. Details of these procedures are found in Reference 18. A comparison of glucoamylase-I (lanes 2 and 5), glucoamylase-II (lanes 3 and 6) and the recombinant glucoamylase (lanes 4 and 7) is shown in FIG. 11. Since the bands corresponding to these proteins also stain with the carbohydrate stain, this demonstrates that the recombinant glucoamylase is glycosylated by the yeast.

EXAMPLE 3

Production of Alcohol from Transformed Yeast

Yeast strain C468 containing pGAC9, and the control C468 yeast strain containing pACI were inoculated into 50 ml of the following medium:

| succinic acid | 11.81 g |
| H₃PO₄ | 0.58 g |
| H₂SO₄ | 0.31 g |
| KCl | 0.37 g |
| NaCl | 58.4 mg |
| MgCl₂.6H₂O | 0.2 g |
| MnSO₄.H₂O | 1.7 mg |
| CuSO₄.5H₂O | 0.25 mg |
| ZnSO₄.7H₂O | 1.44 mg |
| CoCl₂.6H₂O | 1.19 mg |
| Na₂MoO₄.2H₂O | 1.21 mg |
| H₃BO₃ | 3.09 mg |
| CaCl₂.2H₂O | 14.7 mg |
| FeSO₄.7H₂O | 11.1 mg |
| histidine | 40 mg |
| washed soluble starch* | 100 g |
| add water in quantities sufficient to 1 liter | |

*The starch was washed three times in 70% ethanol to remove low molecular weight carbohydrates. The precipitate was then dried, but some ethanol and water may have remained.

*The starch was washed three times in 70% ethanol to remove low molecular weight carbohydrates. The precipitate was then dried, but some ethanol and water may have remained.

Fermentation was carried out in 250 ml flasks which were equipped with air restrictors to restrict the flow of oxygen into the flask. The flasks were incubated at 32° C. and shaken at 200 rpm for 7 days.

The ethanol content of each flask was evaluated using gas chromatography. The C468/pGAC9 culture contained 23.4 g/l ethanol while the control C468/pACI culture contained 4.5 g/l ethanol. The results show that the production of glucoamylase by the C468/pGAC9 culture enabled the strain to convert the soluble starch into glucose and then to ferment the glucose to ethanol.

EXAMPLE 4

Expression of the Glucoamylase Gene in E. coli

In order to express the glucoamylase gene in *E. coli*, a modification was made to the 5' untranslated region in order to make the DNA sequence more compatible with transcription and translation in *E. coli*. Specifically, 27 base pairs between the HindIII site which was constructed 32 base pairs upstream from the ATG initiation codon (see Example 2) and the ATG codon were deleted by oligonucleotide mutagenesis using the procedure described in Example 2B for removal of an intron. The oligonucleotide, which had homology to 12 base pairs on the 5' side of the region to be deleted and 11 base pairs on the 3' side, had the sequence:

5'GAGCCGAAGCTTTATGTCGTTCCG 3'

Except for this deletion, the final HindIII cassette was identical to that constructed for the yeast expression vector in Example 2.

*E. coli* expression vector ptrp3 was constructed by replacing the EcoRI to ClaI region of pBR322 (coordinates −3 to 28, see Reference 16a) with an EcoRI to ClaI fragment containing the *E. coli* tryptophan promoter and ribosome binding site. The nucleotide sequence of this region is shown in Table IV; the EcoRI, ClaI and HindIII sites have been identified in Table IV.

TABLE IV

GAA TTC CGA CAT CAT AAC GGT TCT GGC AAA TAT TCT GAA ATG
EcORI
AGC TGT TGA CAA TTA ATC
ATC GAA CTA GTT AAC TAG TAC GCA AGT TCA CGT AAA AAG GGT
ATC GAT  AAG CTT
ClaI    HindIII The HindIII cassette of the glucoamylase gene, described above in this example, was cloned into the HindIII site of ptrp3. Transformants were screened by DNA restriction fragment mapping in order to identify clones where the glucoamylase gene was in the same orientation as the promoter; one such clone was selected for further study as pGC24.

In order to examine expression of the glucoamylase gene using the trp promoter, plasmid pGC24 was transformed into *E. coli* host MH70 which had been obtained from the *E. coli* Genetic Stock Center, Yale University (their collection number is CGSC 6153). MH70 is a mal⁻ *E. coli* strain whose genotype is araD139, Δ(argF-lac), 205, flbB5301, ptsF25, relAl?, rpsL150, malQ63, bglR15, deoCl? The malQ mutation is in the amylomaltase gene; a mutation in this gene makes *E. coli* unable to hydrolyze maltose to glucose.

A sample of the MH70 transformed with pCG24 was deposited with the American Type Culture Collection on Dec. 16, 1983, and has been assigned the ATCC Deposit No. 39,537.

The MH70/pGC24 transformant and strain MH70 were grown at 37° C. and 200 rpm in 5 ml of the following medium containing tryptophan at 50 mg/1.

| 25X Bonner-Vogel Salts | 40 ml |
|---|---|
| Ampicillin | 50 mg |
| Glucose | 2 g |
| Vitamin B1 | 10 mg |
| Casamino Acid | 2 g |
| Water | to 1000 ml |

25×Bonner-Vogel Salts (*Methods in Enzymology*, XVIIA:5):

| Glass Distilled Water | 670 ml |
|---|---|
| $MgSO_4.7H_2O$ | 5 g |
| Citric Acid.$H_2O$ | 50 g |
| $K_2HPO_4$ | 250 g |
| $NaNH_4PO_4.4H_2O$ | 87.5 g |
| Glass Distilled Water to | 1000 ml |

After overnight incubation, the cells were harvested by centrifugation at 3000g for 5 minutes and resuspended in 5 ml of the same medium but without tryptophan. The cells were then subcultured in 20 ml of the medium without tryptophan to an $A_{660}$ of 0.05-0.07. This culture was grown at 37° C. and 250 rpm to an $A_{660}$ of 0.05. The cells were harvested from 10 ml of culture by centrifugation as above and resuspended in 1 ml of sonication buffer (15% sucrose, 50 mM Tris pH 7, 40 mM EDTA). The samples were sonicated for 3 minutes (on pulsel in a cup sonicator (Sonifier Cell Disrupter #350, Branson Sonic Power Co.). The cell lysates were centrifuged for 5 minutes in an Eppendorf Microfuge and the clear supernatants were removed for further analysis. The clear lysates were electrophoresed on an polyacrylamide SDS gel and analyzed by Western analysis as described in Example 2C. A protein band of approximately 69,000 molecular weight, the size expected for an unglycosylated form of glucoamylase, was detected in the MH70/pGC24 clear lysate but not in the MH70 lysate.

To further demonstrate that an active glucoamylase enzyme was produced in *E. coli*, MH70/pGC24 and MH70 were streaked on MacConkey Agar (Difco Co., Detroit, Mich. 48232) plates containing 1% maltose and incubated overnight at 37° C. The fermentation of maltose results in a pH change in the media that is indicated by a shift from a colorless to red color in the colonies; nonfermenting colonies remain colorless. Since MH70 is malQ−, its colonies were colorless. The expression of the *A. awamori* glucoamylase in NH70/pGC24 permitted the hydrolysis of maltose to glucose and the fermentation of the glucose resulted in red colonies. Therefore, an active glucoamylase is produced in *E. coli*.

While preferred embodiments of the present invention have been described herein, it will be understood that various changes and modifications may be made without departing from the spirit of the invention. For example, while the examples all demonstrate autonomous replication in the host, using integrative transformation of the host as described in References 1c and 1d where the gene and promoter are integrated into the chromosome is also possible.

We claim:

1. A DNA expression vector which comprises:
   a promoter fragment which functions in a host organism, wherein said host organism is yeast;
   and a DNA segment having a modified DNA sequence, greater than 80% free of introns, which codes for glucoamylase protein from *Aspergillus niger*, or which codes for glucoamylase protein from *Aspergillus awamori*;
   the DNA segment being in an orientation with the promoter fragment such that it is expressed in the yeast host to produce a non-native glucoamylase protein.

2. The vector of claim 1 wherein the DNA segment is a cDNA segment.

3. The vector of claim 1 which further comprises a DNA segment which functions as an origin of replication.

4. A yeast, host organism transformed by the expression vector of claim 3.

5. The vector of claim 1 containing no origin of replication.

6. A yeast, host organism transformed by the expression vector of claim 5.

7. The vector of claim 1 which is capable of phenotypic selection in a yeast host.

8. The vector of claim 7 further comprising a selectable marker for selection in the host which is compatible with the host.

9. The vector of claim 8 wherein the selectable marker is LEU2.

10. The vector of claim 1 wherein the promoter fragment is enolase I.

11. The vector of claim 1 further comprising a transcription terminator segment following the modified DNA sequence in the direction of transcription of said coding segment.

12. The vector of claim 11 wherein the transcription terminator segment is from the enolase I gene.

13. The vector of claim 1 wherein the modified DNA sequence has substantially the following DNA sequence, in a 5' to 3' direction:

```
GCG ACC TTG GAT TCA TGG TTG AGC AAC GAA GCG ACC GTG GCT CGT
ACT GCC ATC CTG AAT AAC ATC GGG GCG GAC GGT GCT TGG GTG TCG
GGC GCG GAC TCT GGC ATT GTC GTT GCT AGT CCC AGC ACG GAT AAC
CCG GAC TAC TTC TAC ACC TGG ACT CGC GAC TCT GGT CTC GTC CTC
AAG ACC CTC GTC GAT CTC TTC CGA AAT GGA GAT ACC AGT CTC CTC
TCC ACC ATT GAG AAC TAC ATC TCC GCC CAG GCA ATT GTC CAG GGT
ATC AGT AAC CCC TCT GGT GAT CTG TCC AGC GGC GCT GGT CTC GGT GAA
CCC AAG TTC AAT GTC GAT GAG ACT GCC TAC ACT GGT TCT TGG GGA
CGG CCG CAG CGA GAT GGT CCG GCT CTG AGA GCA ACT GCT ATG ATC
GGC TTC GGG CAA TGG CTG CTT GAC AAT GGC TAC ACC AGC ACC GCA
ACG GAC ATT GTT TGG CCC CTC GTT AGG AAC GAC CTG TCG TAT GTG
GCT CAA TAC TGG AAC CAG ACA GGA TAT GAT CTC TGG GAA GAA GTC
AAT GGC TCG TCT TTC TTT ACG ATT GCT GTG CAA CAC CGC GCC CTT
GTC GAA GGT AGT GCC TTC GCG ACG GCC GTC GGC TCG TCC TGC TCC
```

-continued
```
TGG TGT GAT TCT CAG GCA CCC GAA ATT CTC TGC TAC CTG CAG TCC
TTC TGG ACC GGC AGC TTC ATT CTG GCC AAC TTC GAT AGC AGC CGT
TCC GGC AAG GAC GCA AAC ACC CTC CTG GGA AGC ATC CAC ACC TTT
GAT CCT GAG GCC GCA TGC GAC GAC TCC ACC TTC CAG CCC TGC TCC
CCG CGC GCG CTC GCC AAC CAC AAG GAG GTT GTA GAC TCT TTC CGC
TCA ATC TAT ACC CTC AAC GAT GGT CTC AGT GAC AGC GAG GCT GTT
GCG GTG GGT CGG TAC CCT GAG GAC ACG TAC TAC AAC GGC AAC CCG
TGG TTC CTG TGC ACC TTG GCT GCC GCA GAG CAG TTG TAC GAT GCT
CTA TAC CAG TGG GAC AAG CAG GGG TCG TTG GAG GTC ACA GAT GTG
TCG CTG GAC TTC TTC AAG GCA CTG TAC AGC GAT GCT GCT ACT GGC
ACC TAC TCT TCG TCC AGT TCG ACT TAT AGT AGC ATT GTA GAT GCC
GTG AAG ACT TTC GCC GAT GGC TTC GTC TCT ATT GTG GAA ACT CAC
GCC GCA AGC AAC GGC TCC ATG TCC GAG CAA TAC GAC AAG TCT GAT
GGC GAG CAG CTT TCC GCT CGC GAC CTG ACC TGG TCT TAT GCT GCT
CTG CTG ACC GCC AAC AAC CGT CGT ACC TCC GTC GTG CCT GCT TCT
TGG GGC GAG ACC TCT GCC AGC AGC GTG CCC GGC ACC TGT GCG GCC
ACA TCT GCC ATT CGT ACC TAC AGC AGT GTG ACT GTC ACC TCG TGG
CCG AGT ATC GTG GCT ACT GGC GGC ACC ACT ACG ACG GCT ACC CCC
ACT GGA TCC GGC AGC GTG ACC TCG ACC AGC AAG ACC ACC GCG ACT
GCT AGC AAG ACC AGC ACC AGT ACG TCA TCA ACC TCC TGT ACC ACT
CCC ACC GCC GTG GCT GTG ACT TTC GAT CTG ACA GCT ACC ACC ACC
TAC GGC GAG AAC ATC TAC CTG GTC GGA TCG ATC TCT CAG CTG GGT
GAC TGG GAA ACC AGC GAC GGC ATA GCT CTG AGT GCT GAC AAG TAC
ACT TCC AGC GAC CCG CTC TGG TAT GTC ACT GTG ACT CTG CCG GCT
GGT GAG TCG TTT GAG TAC AAG TTT ATC CGC ATT GAG AGC GAT GAC
TCC GTG GAG TGG GAG AGT GAT CCC AAC CGA GAA TAC ACC GTT CCT
CAG GCG TGC GGA ACG TCG ACC GCG ACG GTG ACT GAC ACC TGG CGG
```

14. The vector of claim 1 further comprising a region adjoining the 5'-end of said modified DNA sequence, which region encodes a signal sequence.

15. The vector of claim 14 wherein the signal sequence is substantially the following amino acid sequence:

MET SER PHE ARG SER LEU LEU ALA LEU SER GLY
LEU VAL CYS THR GLY LEU ALA ASN
VAL ILE SER LYS ARG.

16. The vector of claim 1 which is a plasmid.

17. The vector of claim 16 which is pGAC9.

18. A yeast host transformed by the expression vector of claim 17.

19. The yeast host of claim 18 wherein the yeast is of the strain C468.

20. A yeast host organism transformed by the expression vector of claim 1.

21. The host of claim 1 wherein the yeast is a species of the genus *Saccharomyces*.

22. The host of claim 21 wherein the species is *S. cerevesiae*, *S. uvarum* or *S. carlsbergensis*.

23. The host of claim 22 wherein the species is *S. cerevisiae*.

24. The host of claim 23 wherein the *S. cerevisiae* strain is C468.

25. A yeast fermentation broth containing the yeast host of claim 20.

26. A process for generating a fluid composition containing extracellular glucoamylase, which comprises:
providing a yeast host organism, which host is transformed by a DNA expression vector containing a promoter fragment which functions in that organism, a signal sequence having substantially the following amino acid sequence,

MET SER PHE ARG SER LEU
VAL CYS THR GLY LEU ALA

LEU ALA LEU SER GLY LEU
ASN VAL ILE SER LYS ARG, and a DNA segment greater than 80% free of introns, which codes for glucoamylase from *Aspergillus niger* or *Aspergillus awamori*;
growing the host organism so that glucoamylase is expressed; and
recovering secreted glucoamylase.

27. The process of claim 26 wherein the glucoamylase has been immobilized on a suitable inert carrier.

28. The process of claim 27 wherein the glucoamylase has enzymatic activity.

29. The process of claim 27 comprising employing the immobilized enzyme in a saccharification process.

30. A process for generating an ethanol containing liquid composition by simultaneous saccharification and fermentation which comprises:
providing a nonfermentable carbon source which is a substrate for glucoamylase;
providing a yeast host organism transformed by a DNA expression vector, wherein said vector contains a promotor fragment which functions in said host organism and a DNA segment having a modified DNA sequence greater than 80% free of introns, which codes for a glucoamylase protein selected from the group of glucoamylase proteins from *Aspergillus niger* and *Aspergillus awamori*, the DNA segment being in an orientation with the promoter fragment such that it is expressed in the yeast host to produce a non-native glucoamylase protein;
growing the yeas host organism on said substrate so that glucoamylase is expressed and ethanol is produced; and
recovering an ethanol containing liquid composition.

31. The process of claim 30 wherein the DNA segment is a cDNA segment.

32. The process of claim 30 wherein the yeast is of the genus *Saccharomyces*.

33. The process of claim 32 wherein the yeast host is selected from the group consisting of *S. cerevisiae, S. uvarum*, and *S. carlsbergensis*.

34. The process of claim 32 wherein the yeast host is *S. cerevisiae*.

35. The process of claim 33 wherein the DNA expression vector is a plasmid.

36. The process of claim 35 wherein the yeast host is C468 and the plasmid is pGAC9.

37. The process of claim 30 wherein the nonfermentable carbon source is selected from the group consisting of starch and a starch derived oligosaccharide.

38. The process of claim 37 wherein the nonfermentable carbon source is a soluble starch.

* * * * *